(12) United States Patent
Chai et al.

(10) Patent No.: US 8,791,098 B2
(45) Date of Patent: Jul. 29, 2014

(54) BIOACTIVE PRE-TUBULYSINS AND USE THEREOF

(75) Inventors: Yi Chai, Ithaca, NY (US); Angelika Ullrich, Blieskastel (DE); Uli Kazmaier, Homburg (DE); Rolf Müller, Blieskastel (DE)

(73) Assignee: Universitaet des Saarlandes, Saarbruecken (DE)

( * ) Notice: Subject to any disclaimer, the term of this patent is extended or adjusted under 35 U.S.C. 154(b) by 95 days.

(21) Appl. No.: 13/120,497

(22) PCT Filed: Sep. 22, 2009

(86) PCT No.: PCT/EP2009/062282
§ 371 (c)(1),
(2), (4) Date: Jun. 10, 2011

(87) PCT Pub. No.: WO2010/034724
PCT Pub. Date: Apr. 1, 2010

(65) Prior Publication Data
US 2011/0245295 A1    Oct. 6, 2011

(30) Foreign Application Priority Data

Sep. 25, 2008 (EP) .................................. 08165147

(51) Int. Cl.
*A01N 43/40* (2006.01)
*A61K 31/445* (2006.01)
*A01N 43/00* (2006.01)
*A61K 31/33* (2006.01)
*C07D 405/00* (2006.01)

(52) U.S. Cl.
USPC ......................... 514/183; 514/326; 546/209

(58) Field of Classification Search
None
See application file for complete search history.

(56) References Cited

U.S. PATENT DOCUMENTS 7,754,885 B2 *   7/2010   Hoefle et al. .................. 546/208

FOREIGN PATENT DOCUMENTS

WO    WO 2004/046170    *    6/2004
WO    WO 2008/106080    *    9/2008

OTHER PUBLICATIONS

Dorwald. Side reactions in organic synthesis. page IX. 2006.*

* cited by examiner

*Primary Examiner* — Anna Pagonakis
(74) *Attorney, Agent, or Firm* — Norris McLaughlin & Marcus, P.A.

(57) ABSTRACT

The invention relates to bioactive pre-tubulysin derivatives, their preparation and pharmacological use.

7 Claims, 8 Drawing Sheets

Effect of glycerol-tubulysin on the growth of U937 cells

BIOACTIVE PRE-TUBULYSINS AND USE THEREOF

This application is a 371 of PCT/EP2009/062282, filed Sep. 22, 2009, which claims foreign priority benefit under 35 U.S.C. §119 of the European Patent Application No. 08165147.3 filed Sep. 25, 2008.

The invention relates to bioactive pre-tubulysin derivatives, their preparation and pharmacological use.

BACKGROUND OF THE INVENTION

Tubulysins A and D are members of a group of antimitotic peptides that were originally isolated form the myxobacterial strains Archangium gephyra and Angiococcus disciformis. Both compounds inhibit the growth of cancer cell lines at very low concentrations, whereby tubulysin D is approximately 10 folds more potent than tubulysin A. Treatment of mammalian cells with tubulysins induces a cell cycle arrest at the $G_2M$ phase that followed by induction of apoptosis (Khalil, M. et al., Chembiochem. 7, 678-683 (2006); Sasse, F. et al., Nat. Chem. Biol. 3, 87-89 (2007)). In vitro both drugs inhibit the polymerization of purified microtubule protein and induce the de-polymerization of preassembled microtubules. Previous report demonstrated that tubulysin A strongly interfered with the binding of vinblastine to tubulin in a non-competitive manner (Khalil, M. et al., Chembiochem. 7, 678-683 (2006)).

Certain tubulysin derivatives designated "pretubulysins" were known in the art were firstly observed in extracts from myxobacteria (structures see below). Later they could be chemically synthesized by the Kazmaier group at UDS. For example WO 2008/106080 discloses such pretubulysins having an optionally acylated hydroxyl residue in the central thiazol-containing amino acid residue and/or having an unsaturated C-terminal amino acid residue; and WO2004/046170 mentions fully saturated pretubulysins. However, the apoptotic and cytotoxic activity of these pretubulysins is significant inferior to tubulysin A and D. As the natural abundance of tubulysin A and D is moderate and a synthetic process is not available, there is a strong demand for alternative substances having comparable activity as tubulysin A and D.

SUMMARY OF THE INVENTION

A new class of pretubulysins was found that which show a potent anti-mitotic activity and anti-proliferation effect on different cancer cell lines at low concentration. They induced the de-polymerization of microtubules in PtK2 cells and also of purified microtubules proteins, and inhibit the polymerization of purified microtubules proteins in vitro in a concentration dependent manner. Furthermore, treatment of the cervices carcinoma cell line KB.3.1 or the human acute myeloid leukaemia cell line HL-60 with pre-tubulysin-816 or -827 lead to accumulation of cells in $G_2M$-phase of the cell cycle and induction of apoptosis. However, immunofluorescence studies suggested on some fine differences between their modes of action and that of the natural products tubulysin A and D. These compounds are far more potent than the pretubulysins known so far. The invention thus provides (1) a pre-tubulysin compound having the formula I or II

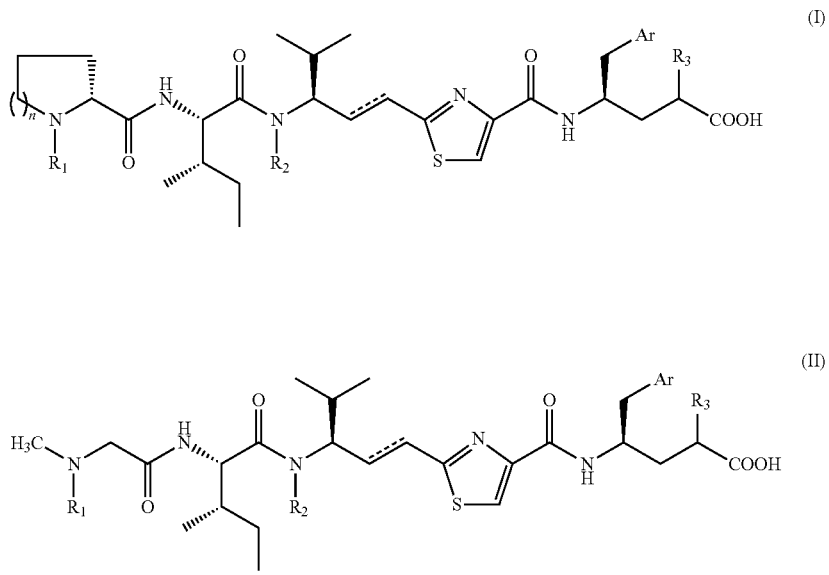

wherein $R_1$ is a branched or linear, saturated or unsaturated $C_{1-6}$ alkyl group which may carry 1 to 3 substituents independently selected from phenyl, halogen, $C_{1-3}$-alkoxy and phenoxy;

$R_2$ is H or a branched or linear, saturated or unsaturated $C_{1-16}$ alkyl group which may carry 1 to 3 substituents independently selected from phenyl, halogen, $C_{1-3}$-alkoxy and phenoxy;

$R_3$ is H or a branched or linear, saturated or unsaturated $C_{1-6}$ alkyl group which may carry 1 to 3 substituents independently selected from phenyl, halogen, $C_{1-3}$-alkoxy and phenoxy;

Ar is phenyl or naphthyl group which may carry 1 to 3 substituents independently selected from $C_{1-3}$-alkyl, $C_{1-3}$-alkenyl, halogen, $C_{1-3}$-alkoxy and $C_{1-3}$-alkenoxy;

n is an integer of 0 to 2 and

------ denotes a single or double bond, or an ester of the C-terminal carboxy group and/or pharmaceutically acceptable salt thereof;

(2) a preferred embodiment of (1) above, wherein ------ denotes a single bond, preferably the compound is pre-tubulysin-827, 816 or 825 or a glycerolester thereof, notably the following compound

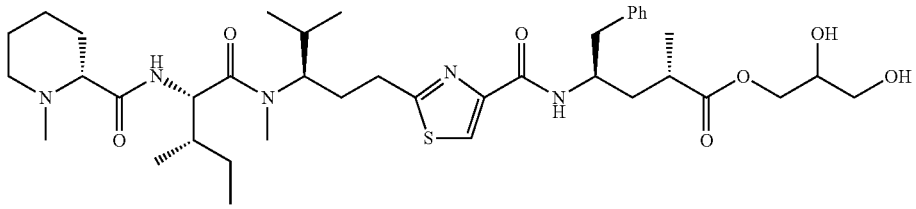 [SMILES: CC[C@H](C)[C@H](NC(=O)[C@H]1CCCCN1C)C(=O)N(C)[C@H](CCc1nc(C(=O)N[C@@H](Cc2ccccc2)C[C@H](C)C(=O)OCC(O)CO)cs1)C(C)C]

(3) a pharmaceutical composition or medicament comprising the compound of (1) or (2) above;
(4) a process for preparing the compound of (1) or (2) above, which comprises condensing the "tubuvaline" and "tubuphenylalanine" building blocks (2) and (3) or the respective derivatives thereof

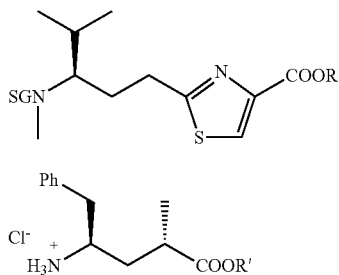

wherein SG, R and R' are appropriate protecting groups;
(5) use of the compound of (1) or (2) above, for preparing a medicament for the treatment of cancer;
(6) a method for the treatment of cancer in a patient which comprises administering the patient a suitable amount of the compound of (1) or (2) above.

SHORT DESCRIPTION OF THE FIGURES

FIG. 3 shows the effect of the glycerol derivative on the growth of the lymphoma cell line U937.

FIG. 4 shows microtubules of the PtK2 cells during interphase (A), and control PtK2-cells during mitosis (B).

Figure 5:
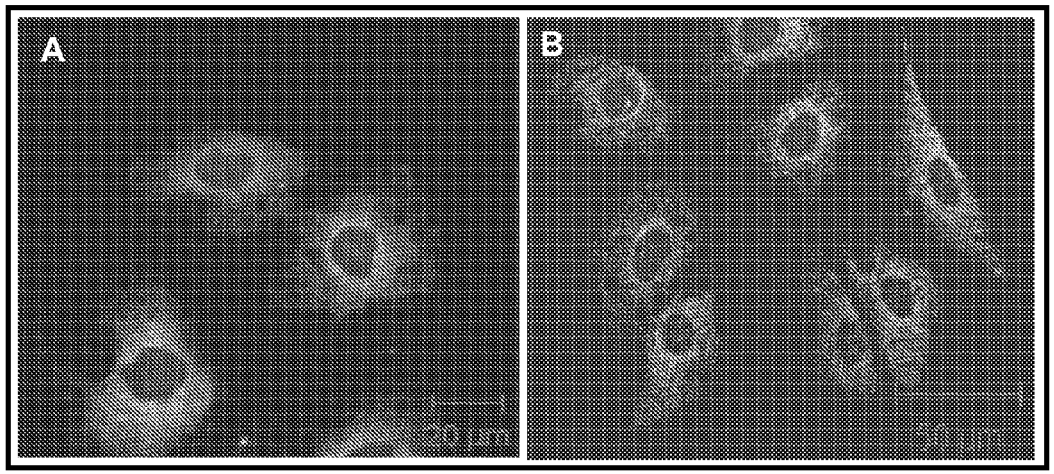

FIG. 5 shows the effect of tubulysin A (A) and tubulysin D (B) on the microtubules structures of PtK2 cells. Cells were treated either with 500 pg/ml tubulysin A or 50 pg/ml tubulysin D for 24 h. The microtubules (green) were then visualized using immunofluorescence. The nuclei were DAPI stained (blue).

Figure 6:
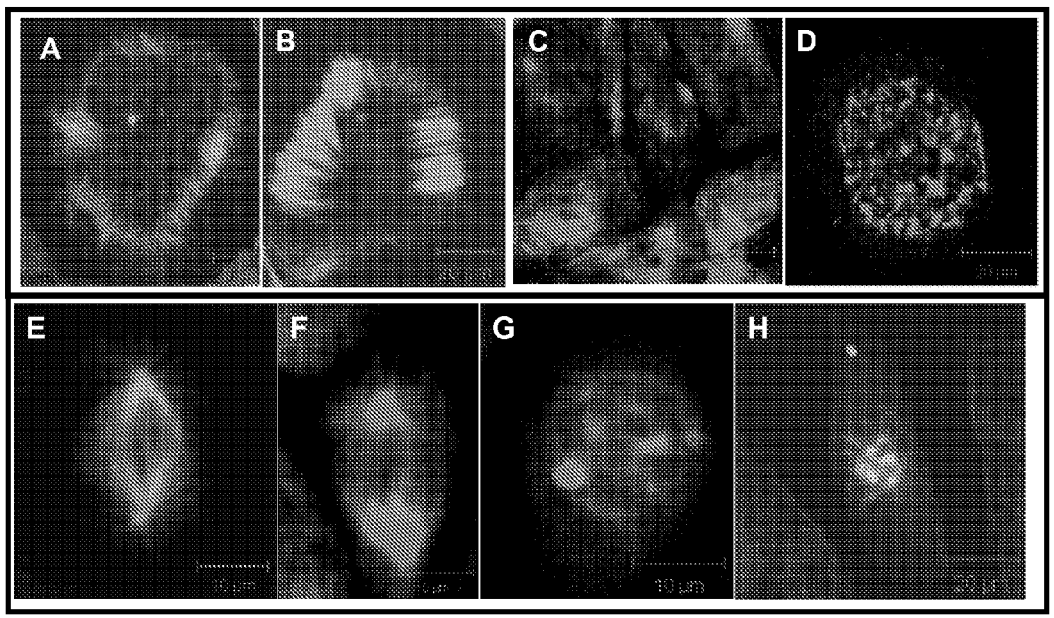

FIG. 6 shows the effect of pre-tubulysin-816 on the microtubules and the spindle apparatus of Ptk2 cells. PtK2 cells were treated with 0.5 (A), 1 (B), 2.5 (C) and 5 (D) µg/ml pre-tubulysi-816 for 24 h. The microtubules became shorter and denser especially near the cell periphery. At a concentration of 100 ng/ml the spindle pool of the treated cells showed no morphological changes (E). At concentration of 250 ng/ml some spindle apparatus are still looking normal (F) and other have more than 2 pools (G). At concentrations equal to or greater than 500 ng/ml most of mitosis cells showed abnormal spindle apparatus (H).

Figure 7:
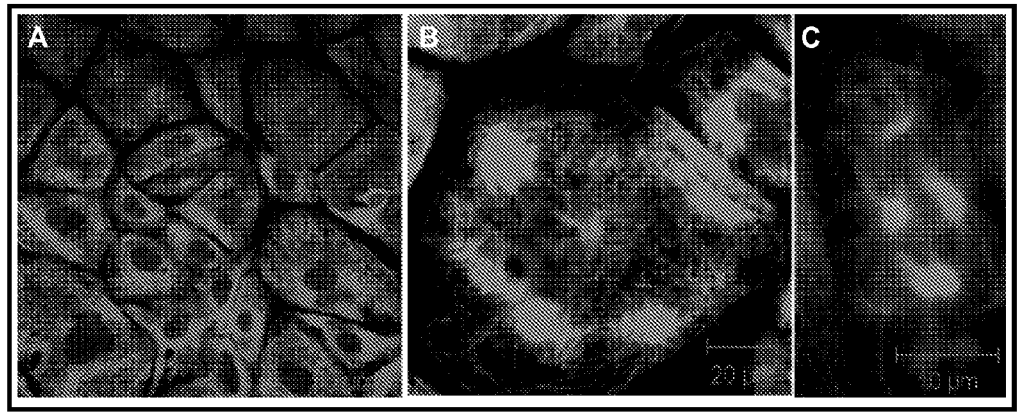

FIG. 7 shows the effect of pre-tubulysin-827 on the microtubules and the spindle apparatus of Ptk2 cells. PtK2 cells were treated with 50 ng/ml for 24 h. (A) and (B) show the effect of pre-tubulysin-827 on the interphase microtubules of PtK2 cells, (C) shows an abnormal spindle apparatus.

Figure 8:
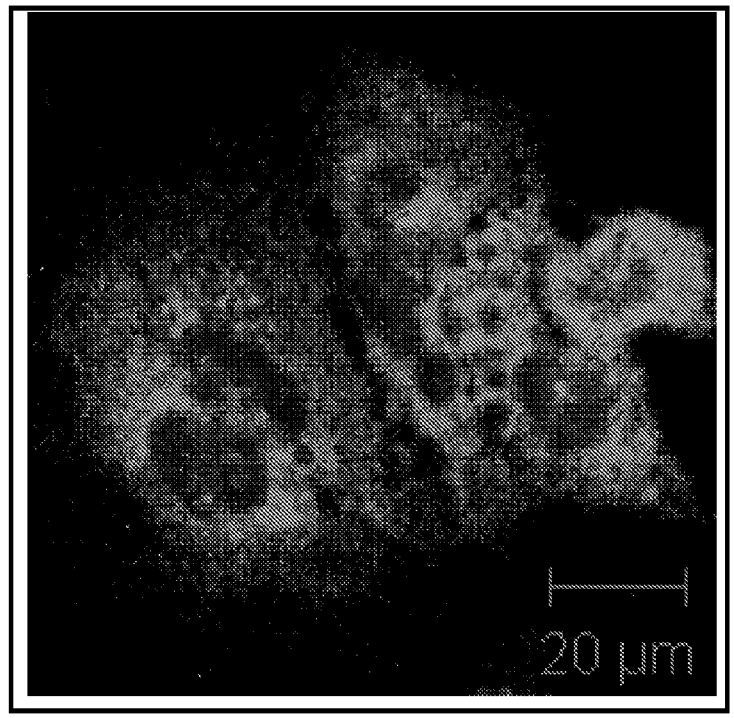

FIG. 8 shows the effect of pre-tubulysin-827 (1 µg/ml) on the interphase microtubules of Ptk2 cells.

Figure 9:
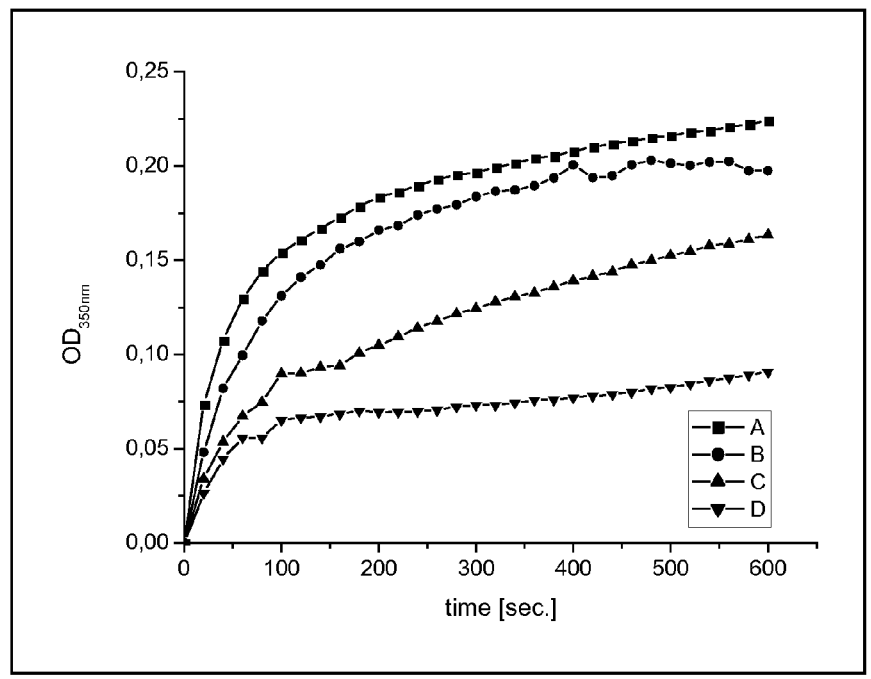

FIG. 9 shows the influences of pre-tubulysin-816 on microtubules protein polymerization in vitro. Microtubules protein (10 µM) were polymerized in the absence (A), and the presence of 1.7 µM (B), 3.2 µM (C), and 6.7 µM pre-tubulysin 816 (D).

Figure 10:
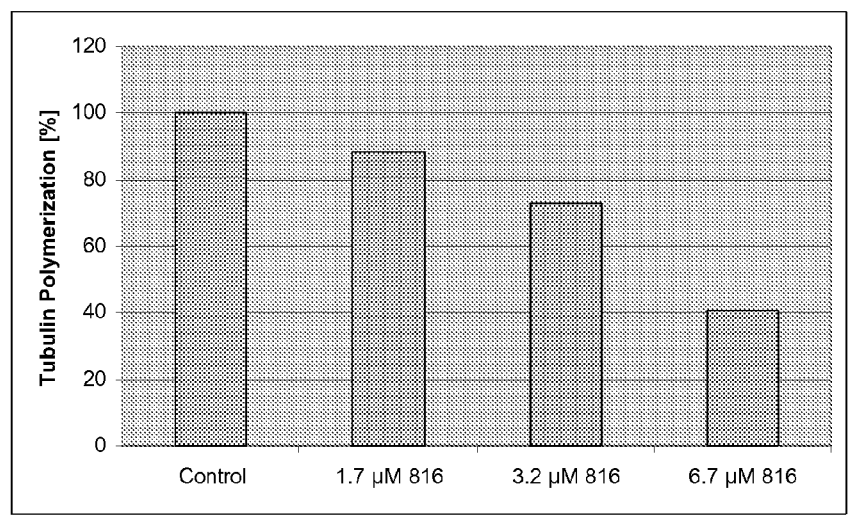

FIG. 10 shows the effect of different concentrations of pre-tubulysin-816 on the microtubules protein polymerization as a percent of the control. The values demonstrated here were calculated from the previous curve (FIG. 9) and represent the values measured after 10 min of incubation with different concentration of the drug at 37° C.

Figure 11:
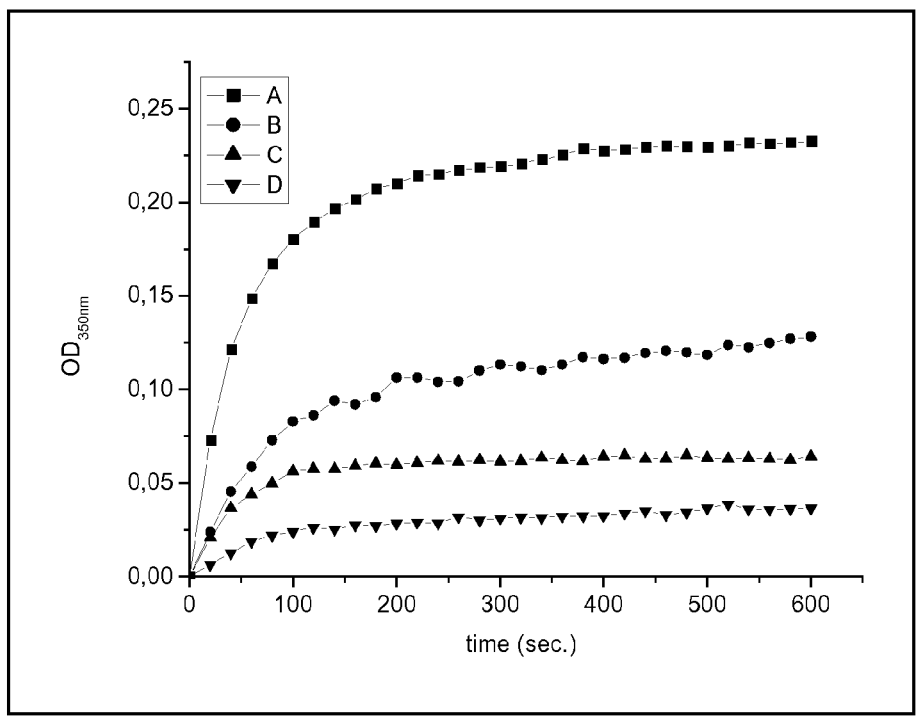

FIG. 11 shows the influences of pre-tubulysin-827 on microtubules protein polymerization in vitro. Microtubules protein (10 µM) were polymerized in the absence (A), and the presence 1 µM (B), 1.7 µM (C), and 3.4 µM pre-tubulysin-827 (D).

Figure 12:
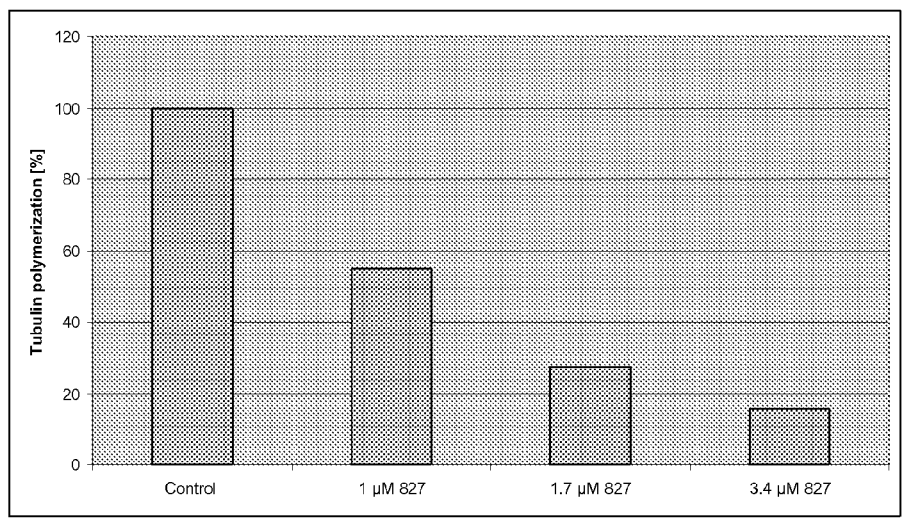

FIG. 12 shows the effect of different concentrations of pre-tubulysin-827 on the microtubules protein polymerization as a percent of the control. The values demonstrated here were calculated from the previous curve (FIG. 11) and represent the values measured after 10 min of incubation with different concentrations of the drug at 37° C.

Figure 13:
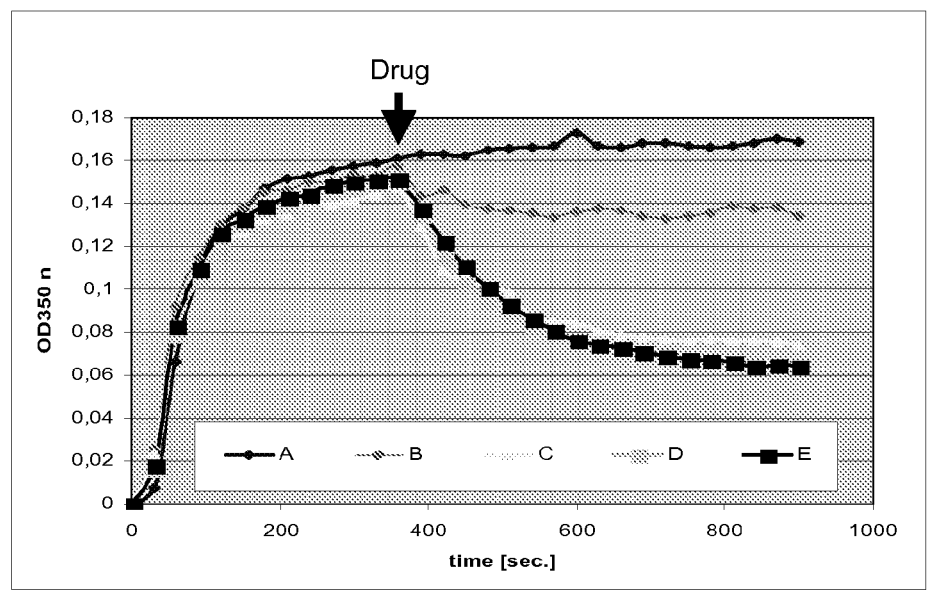

FIG. 13: Pre-tubulysin-827 induces de-polymerization of preassembled microtubules. Microtubules proteins were allowed to polymerize for 5 min at 37° C. 0 µM (A), 1.5 (B), 2.25 µM (C), 3 µM (D) and 3.75 µM pre-tubulysin-827 were added and the stability of the microtubules were monitored for further 10 min.

Figure 14:
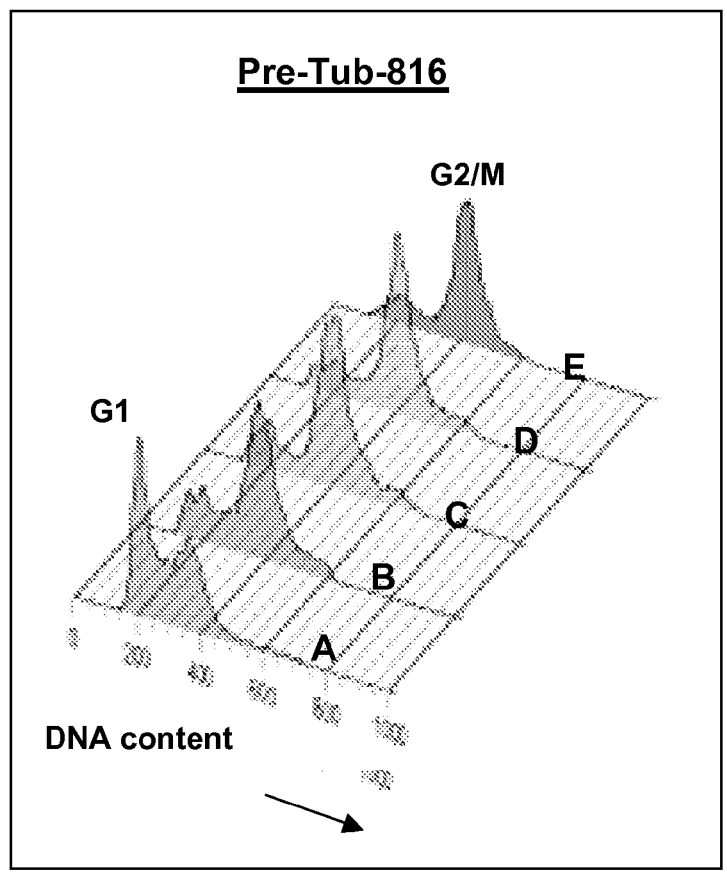

FIG. 14: Pre-tubulysin-816 induces G2M arrest in KB3.1. cells. Cells were treated with 0 (A), 0.2 (B), 0.5 (C), 0.75 (D) and 1 µg/ml (E) for 24 h.

Figure 15:
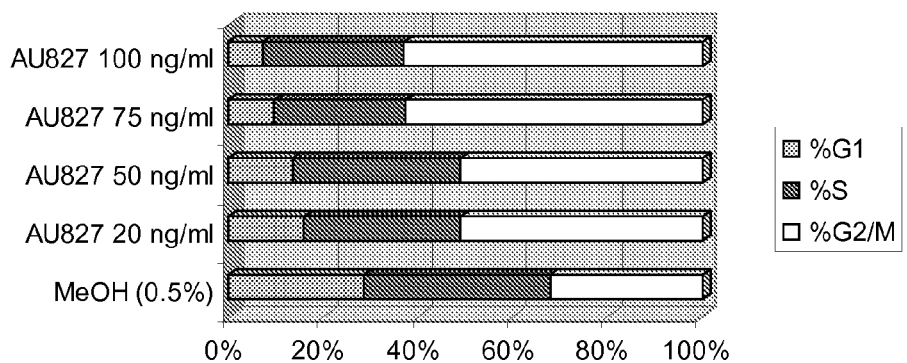

FIG. 15 shows the effect of pre-tubulysin-827 on the cell cycle distribution in KB3.1 cells. Cells were treated with different concentration of the drug for 24 hours. Approximately 30% of the control cells were distributed within the $G_2M$-phase of the cell cycle. After treatment the cells for 24 h with 100 ng/ml pre-tubulysin-827, 65% of the cells accumulated in the $G_2M$-phase.

Figure 16:
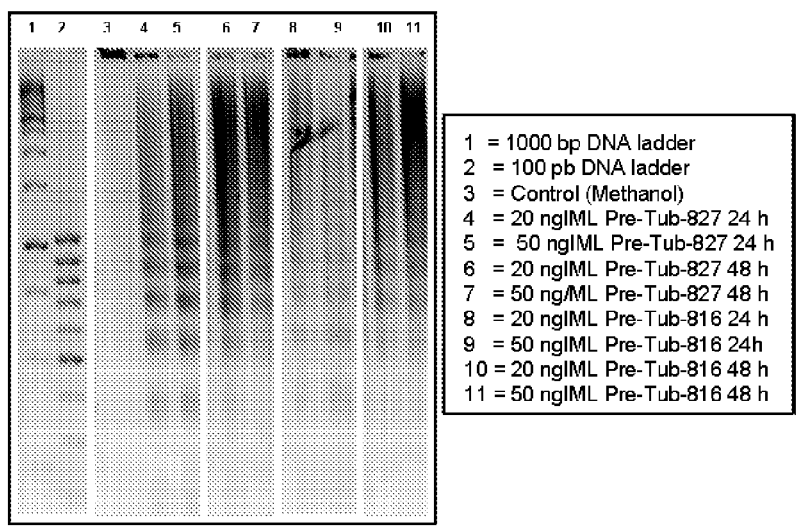

FIG. 16: Pre-tubulysin-816 and -827 induce apoptosis in HL-60 cells characterized by DNA-laddering

DETAILED DESCRIPTION OF THE INVENTION

In the pre-tubulysins of aspect (1) of the invention the variables have the following meanings:

The "branched or linear, saturated or unsaturated $C_{1-6}$ alkyl groups" in the definition of $R_1$ and $R_3$ include methyl, ethyl, n-propyl, iso-propyl, n-butyl, sec-butyl, tert-butyl groups and so on, as well as the respective unsaturated groups having 1, 2 or 3 double bonds. Among said $C_{1-6}$ alkyl groups, the $C_{1-3}$ alkyl and $C_{1-3}$ alkenyl groups are particularly preferred. The "branched or linear, saturated or unsaturated $C_{1-16}$ alkyl group" in the definition of $R_2$ includes similar groups as the $C_{1-6}$ alkyl groups above, the number of double bonds may however be higher. Among said $C_{1-16}$ alkyl groups, the $C_{1-12}$ alkyl and $C_{1-12}$ alkenyl groups are particularly preferred. Even more preferred are the $C_{1-6}$ alkyl and $C_{1-6}$ alkenyl groups.

The optional substituents of said $C_{1-6}$ and $C_{1-16}$ alkyl groups are selected from phenyl, halogen, $C_{1-3}$-alkoxy and phenoxy. "Halogen" includes F, Cl, Br and I, and "$C_{1-3}$-alkoxy" includes methoxy, ethoxy, n-propoxy and iso-propoxy groups.

The Ar groups which may carry 1 to 3 substituents independently selected from $C_{1-3}$-alkyl, $C_{1-3}$-alkenyl, halogen, $C_{1-3}$-alkoxy and $C_{1-3}$-alkenoxy, as to the meaning of The alcohol component of the ester of the C-terminal carboxy group includes mono- and polyhydric alcohols, preferably the alcohol component is selected from $C_1$-alkanols (i.e., alcohols of the $C_{1-6}$ alkyl radicals defined above), $C_{1-6}$-alkenols (i.e., alcohols of the respective unsaturated radicals), $C_{2-6}$-alkylendiols (including ethylenglycol, 1,2- and 1,3-propylenglycol, 1,4-butylenglycol, etc.) and glycerol. "Pharmaceutically acceptable salts" include hydrochlorides, sulphates, phosphates, ammonium salts and so on.

Particularly preferred compounds of aspect (1) of the invention are compounds wherein $R_1$ is a methyl, ethyl, propyl, benzyl or allyl group. Further preferred compounds of aspect (1) of the invention are compounds wherein $R_2$ is H, a $C_{1-12}$-alkyl group, a benzyl group or an allyl group.

Even further preferred compounds of aspect (1) of the invention are compounds wherein $R_3$ is H, a methyl, ethyl, allyl or benzyl group.

Still further preferred compounds of aspect (1) of the invention are compounds wherein Ar is an unsubstituted phenyl group

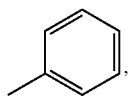

a substituted phenyl group

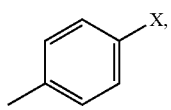

or a substituted naphthyl group

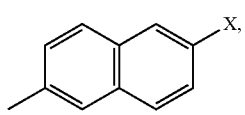

wherein X is selected from —$CH_3$, —$OCH_3$, -allyl, -Oallyl and halogen.

Still further preferred compounds of aspect (1) of the invention are compounds wherein n is 1 or 2.

The pharmaceutical composition or medicament of aspects (3) and (5) of the invention may further contain pharmaceutically acceptable carriers, binders, diluents, and the like.

The synthesis of aspect (4) of the invention is hereinafter shown in connection with the pre-tubulysin (1).

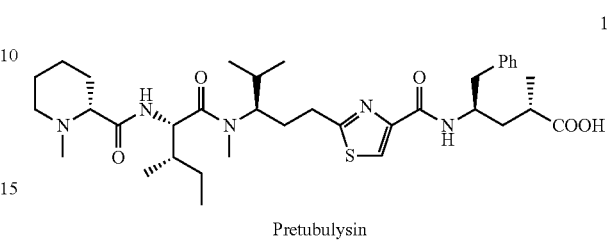

Pretubulysin

As a core step it comprises the synthesis of the building blocks "tubuvaline" and "tubuphenylalanine", components (2) and (3):

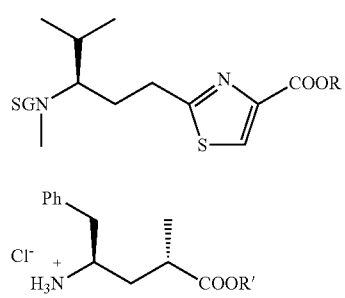

The "tubuvaline" (2) is prepared according to the following reaction scheme:

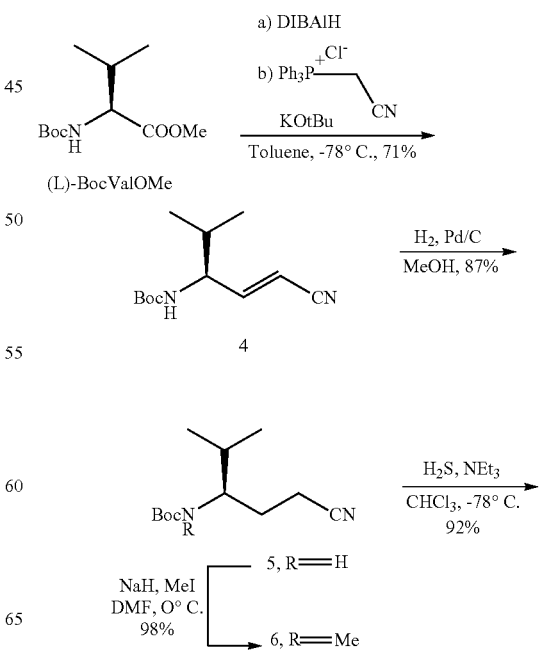

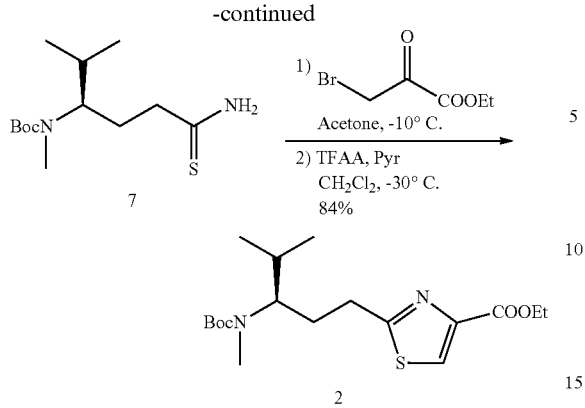
The "tubuphenylalanine" (3) is prepared according to the following reaction scheme:
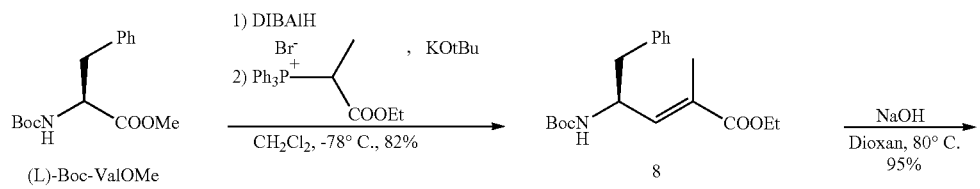
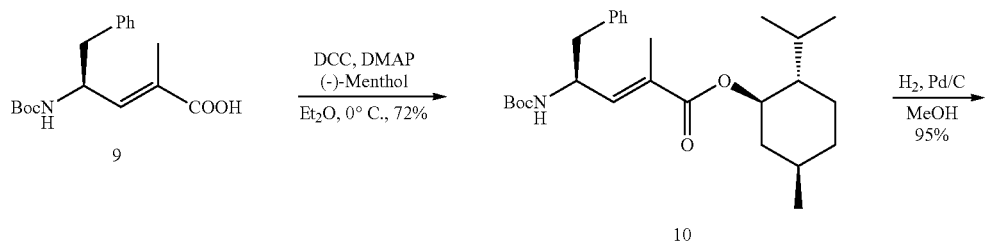
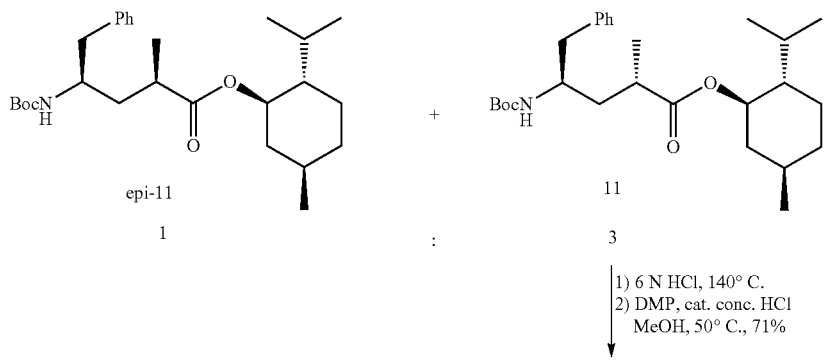
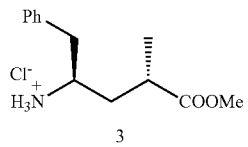

The synthesis of the tetrapeptide pre-tubulysin (1) is then effected according to the following reaction scheme:

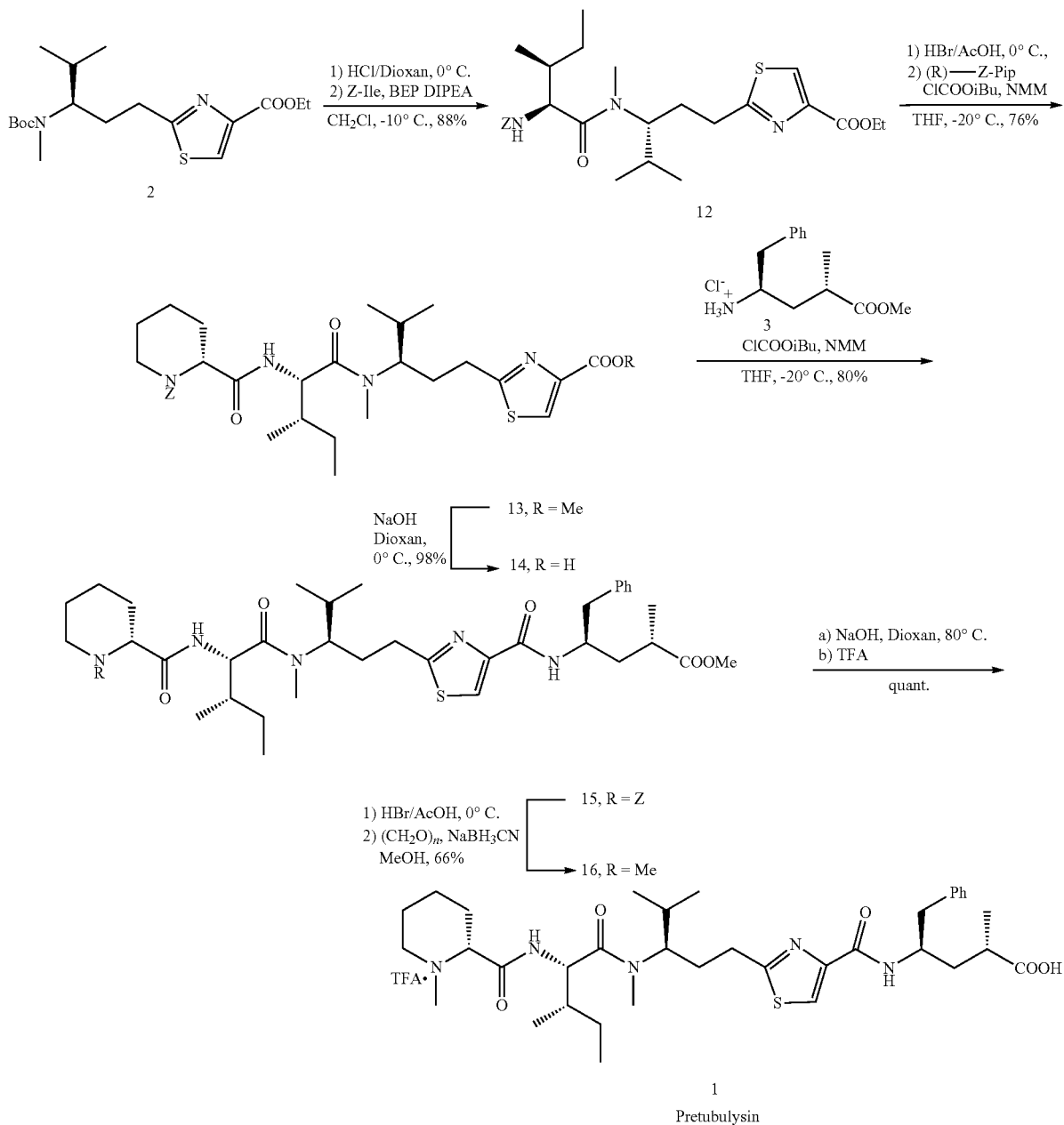

In the appending examples it was tested effect of different pre-tubulysin derivatives on the growth of different cancer cell lines as well as on purified microtubules proteins in vitro. Our results showed that, 2 of the tested substances (pre-tub-816 and -827) showed high anti-proliferation activities against most tested cell lines, whereby pre-tub-827 was at least 5-10 folds more potent than pre-tub-816. Pre-tub-815 and -825 were also active but at higher drug concentration. In comparison Pre-tub-814 did not show any cytotoxic activity at concentration up to 11 μg/ml. Immunofluorescence investigations showed that treatment the PtK2 cells with pre-tubulysins induced at high concentrations (μg level) a de-polymerization of interphase microtubules. This characteristic morphology is compatible to that caused by tubulysin A or D but at much lower concentrations (pg to ng level). However, at lower drug concentrations (ng level) induce the pre-tubulysins a unique morphology of the interphase microtubules. The microtubules here seem to be shorter and more dense, especially around the periphery of the cell. To our knowledge, these morphologies have not been seen by other anti-mitotic drugs that induce microtubules de-polymerization (e.g. disorazol, tubulysin and or vinblastine). These findings suggest a novel mechanism by which pre-tubulysins interact with tubulin and/or microtubules.

Like other anti-mitotic agents pre-tubulysin induced G2M arrest of the cell cycle, followed by induction of apoptosis. This could be indicated via DNA-laddering of the treated cells. Pre-tubulysins are promising anti-mitotic drugs that can be chemically synthesized and produced in large amount. Especially pre-tub-827 is equivalent in action to the natural products tubulysin A and D.

The invention is further described in the following examples, which are, however, not to be construed as limiting the invention.

EXAMPLES

Materials and Methods

Cell cultures: Cell lines were obtained from the American Type Culture Collection and the German Collection of Microorganisms and Cell Cultures. The cell lines were cultured under conditions by their respective depositors. Cell culture reagents were purchased from Life Technologies Inc (GIBCO BRL). Plastic ware was obtained from Nunc and Saarstedt.

Cell staining: $Ptk_2$ cells were seeded on round glass coverslips (13 mm in diameter) in 4-well plates. Cells were incubated with the drugs to the given times as indicated for each experiment. For staining the microtubules and the nuclei, cells were firstly fixed with cold (−20° C.) acetone/methanol (1:1) for 10 min. For labelling the microtubules, cells were incubated with a primary monoclonal antibody against α-tubulin (1:500 Sigam) for 45 min at 37° C., followed by a secondary anti-mouse IgG antibody conjugated with Alexa488 (1:2000; Molecular probes) under the same incubations conditions. The nuclei were stained with DAPI (1 µg/ml in PBS). The cells were washed with phosphate buffer saline (PBS) between incubations. Coverslips were mounted by using Prolong Antifade (Molecular Probes) and imaged through a fluorescence microscope (LSM-Zeiss) with appropriate filter set.

Cell cycle analysis: approximately $10^6$ cells were harvested by centrifugation and fixed in −20° C. cold 80% methanol. After 30 min of incubation on ice, the cells were washed with PBS and then with saponin containing PBS (0.1%). For DNA staining cells were incubated for 30 min at 37° C. in a solution containing 20 µg ml$^{-1}$ Propidium iodide, and 1 mg ml$^{-1}$ RNase. Samples were analysed by FacScan (Becton Dickinson).

Detection of DNA laddering: Apoptotic DNA fragmentation was investigated using the method described by Gong et al. 1-2 µg DNA were loaded into a well of a 1.7% agarose gel, separated by electrophoresis at 4 volts/cm for approximately 4 hours using 0.5×TBE buffer (0.045 M Tris-borate, 1 mM EDTA). The resulting bands were stained by ethidium bromide and detected under UV-light.

Tubulin purification: Microtubules proteins were purified from porcine brain by using standard procedures that includes three cycles of temperature-dependent polymerization and de-polymerization, as described elsewhere.

Polymerisation assay: Tubulin polymerisation was monitored by using turbidometry assay (lit). Samples (200 µl, 10 µM tubulin) in PEM polymerisation buffer (0.1 M PIPES, pH 6.6, 1 mM EGTA, 1 mM $MgSO_4$, and 1 mM GTP), were rapidly warmed to 37° C. in a water-jacketed cuvette holder of a diode array photometer (Beckman spectrophotometer DU 7500). Absorbance at 350 nm where monitored in the absence and the presence of the drugs.

Electron Microscopy Tubulin samples (10 µM) in PEM-polymerisation buffer were incubated at 37° C. in the presence and the absence of the drugs. The samples were then fixed using formaldehyde to a final concentration of 2%, Samples (10 µl) were adsorbed to carbon-coated copper grids, fixed for 60 s in glutaraldehyde (0.5%), and thin rinsed with distilled water. The grids were negatively contrasted with aqueous uranyl acetate solution (2%). Blotted and dried. The specimens were examined under Zeiss CEM 902 transmission electron microscopy.

Chemical Structures of Pre-tubulysins

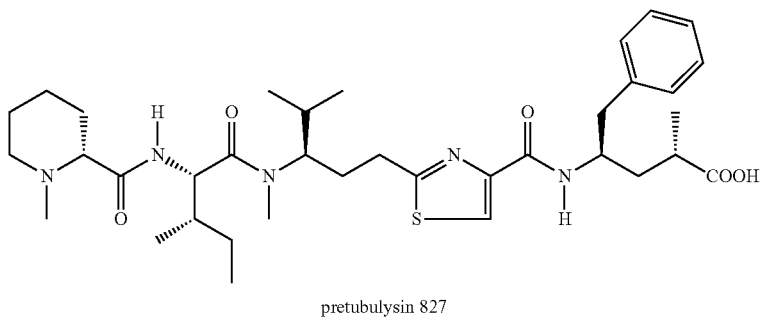

pretubulysin 827

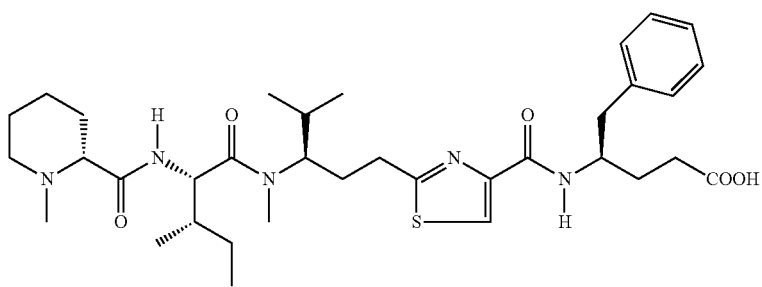

pretubulysin 816

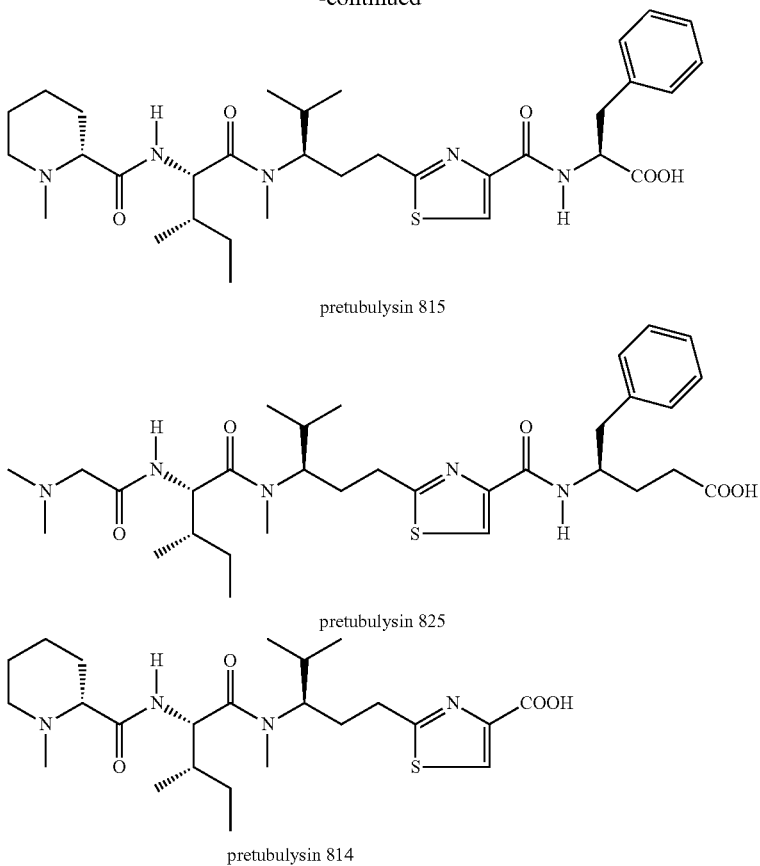

pretubulysin 815 pretubulysin 825 pretubulysin 814

The glycerolester of pre-tubulysin referred to in example 2/FIG. 3 has the following structure:

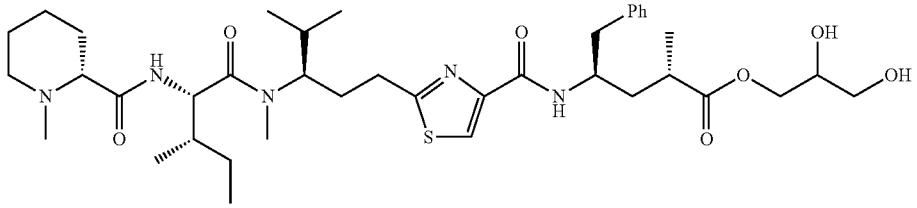 [SMILES: CC[C@H](C)[C@H](NC(=O)[C@H]1CCCCN1C)C(=O)N(C)[C@H](CCc1nc(C(=O)N[C@@H](Cc2ccccc2)C[C@H](C)C(=O)OCC(O)CO)cs1)C(C)C]

Thin-layer chromatography: Polygram SIL G/UV$_{254}$ ready-made sheets from Macherey-Nagel were used. The detection was effected by means of UV light and potassium permanganate as a dipping agent.

Column chromatography: Silica-packed columns were used (MN Kieselgel 60, 0.063-0.2 mm/70-230 mesh ASTM from Macherey-Nagel).

$^1$H NMR spectra were recorded with 500 MHz nuclear magnetic resonance spectrometers (Bruker DRX 500 and Bruker AV 500) and a 400 MHz instrument (Bruker AV 400). Unless stated otherwise, deuterated chloroform was used as the solvent. Calibration was based on the solvent (CDCl$_3$: δ=7.24), and the evaluation was by first order using WinNMR software from Bruker. The abbreviations have the following meanings: s=singlet, d=doublet, t=triplet, q=quartet, m=multiplet, sh=signal cluster, bs=broad singlet, and combinations thereof, such as ddt=doublet of doublet of triplet. The chemical shifts are δ values and are stated in ppm.

$^{13}$C NMR spectra were also recorded with the above mentioned spectrometers (DRX 500 and AV 500: measuring frequency 125 MHz; AV 400: measuring frequency 100 MHz). Calibration was based on the solvent signal (CDCl$_3$: 77.0 ppm). The chemical shifts are stated in ppm, and the measurements were performed with broad-band decoupling. The abbreviations have the following meanings: s=singlet (quaternary carbon atom), d=doublet (CH group), t=triplet (CH$_2$ group), q=quartet (CH$_3$ group). Shifts labeled with * have been estimated from $^{13}$C or HSQC spectra.

Melting points are uncorrected and were measured in open glass capillaries by means of a melting point determination apparatus MEL-TEMP II from Laboratory Devices.

Optical rotations were measured with a polarimeter from PerkinElmer (Model 341) in a thermostatted (20° C.±0.1° C.) 1 dm cuvette. A sodium vapor lamp (λ=589 nm) served as the radiation source. The specific rotation)([α]$_D^{20}$) values were calculated by the measuring apparatus after the concentration has been entered.

Elemental analyses were performed at the Institut für Organische Chemie of the Saarland University by Heike Roeser.

Highly resolved mass spectra (HRMS) were recorded at the Saarland University by Rudi Thomes with a MAT 90 instrument from Finnigan. The fragmentation was achieved by chemical ionization (CI).

Solvents were supplied by the central chemicals store of the Saarland University and distilled before use.

Anhydrous solvents were made absolute by the usual methods: THF over lithium aluminum hydride, diethyl ether and toluene over sodium, dichloromethane over calcium hydride. On principle, experiments with anhydrous solvents were performed under a nitrogen atmosphere in glass equipment previously heated under vacuum to remove volatiles.

Abbreviations: BEP 2-Bromo-1-ethylpyridinium tetrafluoroborate; DCC Dicyclo-hexylcarbodiimide; DIBAlH Di-iso-butylaluminum hydride; DIPEA Di-iso-propyl-ethylamine; DMAP Dimethylaminopyridine; DMF Dimethylformamide; DMP Dimethoxypropane; EE Ethyl acetate; NMM N-Methylmorpholine; Pyr Pyridine; TFA Trifluoroacetic acid; TFAA Trifluoroacetic anhydride; and THF Tetrahydrofuran.

Example 1

Synthesis of Pretubuliysins 1.1. (4S,2E)-4-(tert.-Butoxycarbonylamino)-5-methyl-2-hexenenitrile (4): To a solution of 1.74 g of L-Boc-valine methyl ester (7.52 mmol, 1.0 eq.) in 20 ml of absolute toluene, 15 ml of a 1 M DIBAlH solution (15 mmol, 2.0 eq.) is slowly added dropwise at −78° C. While the reaction mixture is stirred at −78° C. for 30 min, the ylide solution is prepared from 4.67 g of cyanomethyl-triphenylphosphonium chloride (13.8 mmol, 1.8 eq.) and 1.55 g of KOtBu (13.8 mmol, 1.8 eq.) in 15 ml of absolute toluene at room temperature. The ylide is added dropwise to the aldehyde solution at −78° C., and after one hour, the cooling bath is removed, and stirring is performed over night at room temperature.

The reaction mixture is poured into 100 ml of saturated potassium-sodium tartrate solution and stirred vigorously for 30 min. The aqueous phase is extracted with ethyl acetate, and the combined organic phases are dried over $Na_2SO_4$. Purification by column chromatography (hexane:EE 9:1, 8:2) yields 1.20 g of the Wittig product (4) (5.35 mmol, 71% of theory) as a white solid.

$R_f$(4)=0.29 (hexane:EE 8:2)

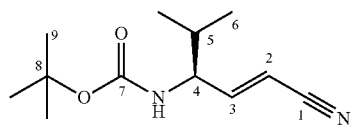 [SMILES: CC(C)[C@@H](/C=C/C#N)NC(=O)OC(C)(C)C]

$^1$H NMR (500 MHz, $CDCl_3$): δ=0.90 (d, $^3J_{6,5}$=6.7 H, 3 H, 6-H), 0.93 (d, $^3J_{6',5}$=6.7 Hz, 1 H, 6'-H), 1.43 (s, 9 H, 9-H), 1.84 (m, 1 H, 5-H), 4.11 (bs, 1 H, 4-H), 4.50 (bs, 1 H, NH), 5.47 (dd, $^3J_{2,3}$=16.5 Hz, $^4J_{2,4}$=1.6 Hz, 1 H, 2-H), 6.62 (dd, $^3J_{3,2}$=16.5 Hz, $^3J_{3,4}$=5.5 Hz, 1 H, 3-H).

$^{13}$C NMR (125 MHz, $CDCl_3$): δ=18.0 (q, C-6), 18.8 (q, C-6'), 28.3 (q, C-9), 32.0 (d, C-5), 57.4 (d, C-4), 80.2 (s, C-8), 100.4 (d, C-2), 117.1 (s, C-1), 154.0 (d, C-3), 155.1 (s, C-7).

Optical rotation: $[α]_D^{20}$=−0.3° (c=1.0 g/100 ml, $CHCl_3$)

Melting point: 62° C.

Elemental analysis:

| $C_{12}H_{20}N_2O_2$ | calc. | C | 64.26 | H | 8.99 | N | 12.49 |
|---|---|---|---|---|---|---|---|
| (224.30) | found | C | 64.04 | H | 9.25 | N | 12.86 |

| HRMS (CI) | calculated | found |
|---|---|---|
| $C_{12}H_{21}N_2O_2$ [M + H]$^+$ | 225.1603 | 225.1536 |

1.2. (4R)-4-(tert.-Butoxycarbonylamino)-5-methyl-hexanenitrile (5): 2.77 g of (4) (12.3 mmol) is stirred with 138 mg of Pd/C (10%) under a hydrogen atmosphere until the reaction is complete (DC control). After the catalyst has been filtered off through Celite and the solution purified by column chromatography (hexane:EE 8:2), 2.41 g of (5) (10.6 mmol, 87% of theory) is obtained as a white solid.

$R_f$(5)=0.19 (hexane:EE 8:2)

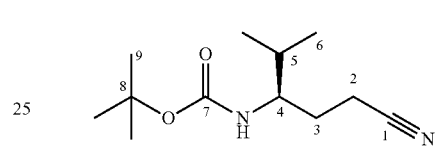

$^1$H NMR (400 MHz, $CDCl_3$): δ=0.88 (d, $^3J_{6,5}$=6.8 Hz, 3 H, 6-H), 0.91 (d, $^3J_{6',5}$=6.8 Hz, 3 H, 6'-H), 1.42 (s, 9 H, 9-H), 1.59 (m, 1 H, 3-H$_a$), 1.71 (m, 1 H, 5-H), 1.89 (m, 1 H, 3-H$_b$), 2.35 (ddd, $^2J_{2a,2b}$=16.9 Hz, $^3J_{2a,3a/b}$=8.3 Hz, $^3J_{2a,3a/b}$=7.0 Hz, 1 H, 2-H$_a$), 2.41 (ddd, $^2J_{2b,2a}$=16.9 Hz, $^3J_{2b,3a/b}$=8.8 Hz, $^3J_{2a,3a/b}$=6.4 Hz, 1 H, 2-H$_b$), 3.43 (dddd, $^3J_{4,3a/b}$≈$^3J_{4,NH}$=10.3 Hz, $^3J_{4,5}$=5.5 Hz, $^3J_{4,3a/b}$=3.5 Hz, 1 H, 4-H), 4.32 (d, $^3J_{NH,4}$=8.8 Hz, 1 H, NH).

$^{13}$C NMR (125 MHz, $CDCl_3$): δ=14.6 (t, C-2), 17.8 (q, C-6), 19.1 (q, C-6'), 28.3 (q, C-9), 29.2 (t, C-3), 32.3 (d, C-5), 55.2 (d, C-4), 79.6 (s, C-8), 119.8 (s, C-1), 156.0 (s, C-7).

Optical rotation: $[α]_D^{20}$=+5.1° (c=1.0 g/100 ml, $CHCl_3$)

Melting point: 65° C.

Elemental analysis:

| $C_{13}H_{24}N_2O_2$ | calc. | C | 63.69 | H | 9.80 | N | 12.38 |
|---|---|---|---|---|---|---|---|
| (226.32) | found | C | 63.62 | H | 9.36 | N | 12.59 |

| HRMS (CI) | calculated | found |
|---|---|---|
| $C_{12}H_{23}N_2O_2$ [M + H]$^+$ | 227.1759 | 227.1814 |

1.3. (4R)-4-(tert.-Butoxycarbonyl-methylamino)-5-methyl-hexanenitrile (6): A solution of 2.39 g of (5) (10.6 mmol) in 40 ml of absolute DMF is admixed with 2.6 ml of methyl iodide (41.8 mmol, 3.9 eq.). At 0° C., a suspension of 964 mg of sodium hydride (55-65%, 22.1-26.1 mmol, 2.1-2.5 eq.) in 10 ml of abs. DMF is added dropwise. The reaction mixture is allowed to warm to room temperature over night, poured into 200 ml of water and 50 ml of saturated ammonium chloride solution, stirred vigorously and then extracted with ethyl acetate. Purification by column chromatography (hexane:EE 8:2) yields 2.51 g of product (6) (10.4 mmol, 98%) as a colorless oil.

$R_f(6)=0.18$ (hexane:EE 8:2)

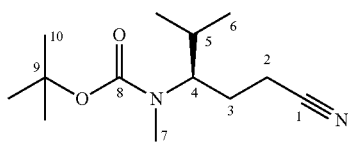 [SMILES: CC(C)[C@@H](CCC#N)N(C)C(=O)OC(C)(C)C]

$^1$H NMR (400 MHz, CDCl$_3$): Ratio of rotamers at room temperature: about 1:1 δ=0.83 (d, $^3J_{6,5}$=7.0 Hz, 3 H, 6-H), 0.85 (d, $^3J_{6,5}$=6.8 Hz, 3 H, 6-H), 0.93 (d, $^3J_{6',5}$=6.5 Hz, 3 H, 6'-H), 0.94 (d, $^3J_{6',5}$=6.5 Hz, 3 H, 6'-H), 1.43 (s, 9 H, 10-H), 1.45 (s, 9 H, 10-H), 1.62-1.75 (sh, 4 H, 3-H$_a$, 5-H), 1.91-2.03 (sh, 2 H, 3-H$_b$), 2.12-2.34 (sh, 4 H, 2-H$_a$, 2-H$_b$), 2.64 (s, 6 H, 7-H), 3.62 (bs, 1 H, 4-H), 3.68 (td, $^3J_{4,3}$=10.8 Hz, $^3J_{4,5}$=3.3 Hz, 1 H, 4-H).

$^{13}$C NMR (100 MHz, CDCl$_3$): δ=14.5 (t, C-2), 19.6, 19.8, 20.0, 20.1 (4 q, C-6, C-6'), 25.9 (t, C-3), 28.4 (q, C-10), 28.8 (q, C-7), 30.3, 30.5 (2 d, C-5), 60.8, 61.1 (2 d, C-4), 79.7, 80.2 (2 s, C-9), 119.3, 119.7 (2 s, C-1), 156.3, 156.6 (2 s, C-8).

Optical rotation: $[\alpha]_D^{20}$=+4.7° (c=1.0 g/100 ml, CHCl$_3$)

| HRMS (CI) | calculated | found |
|---|---|---|
| C$_{13}$H$_{25}$N$_2$O$_2$ [M + H]$^+$ | 241.1916 | 241.1903 |

1.4. (4R)-4-(tert.-Butoxycarbonyl-methylamino)-5-methyl-hexanethioamide (7): Through a solution of 1.85 g of nitrile (6) (7.70 mmol) and 5.4 ml of triethylamine (38.4 mmol, 5.0 eq.) in 15 ml of chloroform, H$_2$S is bubbled at −78° C. for 1 hour. The reaction mixture is tightly sealed, allowed to warm to room temperature over night and stirred at room temperature for several days, during which time it turns to yellow to green. For processing, the mixture is washed with 1 M HCl solution, saturated NaHCO$_3$ solution and water, the organic phase is dried over Na$_2$SO$_4$. Purification by column chromatography (hexane:EE 1:1) yields 1.94 g of thioamide (7) (7.07 mmol, 92% of theory) as a white solid.

$R_f(7)=0.33$ (hexane:EE 1:1)

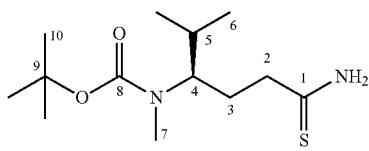 [SMILES: CC(C)[C@@H](CCC(N)=S)N(C)C(=O)OC(C)(C)C]

$^1$H NMR (400 MHz, CDCl$_3$):

Major rotamer: δ=0.82 (d, $^3J_{6,5}$=6.5 Hz, 3 H, 6-H), 0.93 (d, $^3J_{6',5}$=6.8 Hz, 3 H, 6'-H), 1.44 (s, 9 H, 10-H), 1.60 (m, 1 H, 5-H), 1.70 (dddd, $^2J_{3a,3b}$=14.6 Hz, $^3J_{3a,4}$=12.3 Hz, $^3J_{3a,2b}$=6.8 Hz, $^3J_{3a,2a}$=3.5 Hz, 1 H, 3-H$_a$), 2.04 (dddd, $^2J_{3b,3a}$=14.6 Hz, $^3J_{3b,2a}$=11.0 Hz, $^3J_{3b,2b}$≈$^3J_{3b,4}$=3.0 Hz, 1 H, 3-H$_b$), 2.39 (ddd, $^2J_{2a,2b}$=12.6 Hz, $^3J_{2a,3b}$=11.0 Hz, $^3J_{2a,3a}$=3.5 Hz, 1 H, 2-H$_a$), 2.61 (s, 3 H, 7-H), 2.73 (dddd, $^2J_{2b,2a}$=12.6 Hz, $^3J_{2b,3a}$=6.8 Hz, $^3J_{2b,3b}$=3.5 Hz, $^4J_{2b,4}$=1.5 Hz, 1 H, 2-H$_b$), 3.68 (ddd, $^3J_{4,3a}$=12.3 Hz, $^3J_{4,5}$=10.3 Hz, $^3J_{4,3b}$=2.5 Hz, 1 H, 4-H), 7.48 (bs, 1 H, NH), 8.71 (bs, 1 H, NH').

Selected signals of the minor rotamer: δ=1.42 (s, 9 H, 10-H), 2.24 (m, 1 H, 3-H$_b$), 2.43-2.57 (sh, 2 H, 2-H$_a$, 2-H$_b$), 2.65 (s, 3 H, 7-H), 3.61 (bs, 1 H, 4-H).

$^{13}$C NMR (100 MHz, CDCl$_3$):

Major rotamer: δ=19.9 (q, C-6), 20.2 (q, C-6'), 27.9 (q, C-7), 28.4 (q, C-10), 28.7 (t, C-3), 29.8 (d, C-5), 41.9 (t, C-2), 60.0 (d, C-4), 80.2 (s, C-9), 158.0 (s, C-8), 210.4 (s, C-1).

Selected signals of the minor rotamer: δ=19.9 (q, C-6), 28.5 (q, C-10), 41.5 (t, C-2), 79.8 (s, C-9), 153.3 (s, C-8), 211.6 (s, C-1).

Optical rotation: $[\alpha]_D^{20}$=+19.7° (c=1.0 g/100 ml, CHCl$_3$)

| HRMS (CI) | calculated | found |
|---|---|---|
| C$_{13}$H$_{27}$N$_2$O$_2$S [M + H]$^+$ | 275.1793 | 275.1769 |

1.5. (R)-2-[3-(tert.-Butoxycarbonyl-methylamino)-4-methyl-pentyl]-thiazole-4-carboxylic acid ethyl ester (2): To a solution of 1.37 g of thioamide (7) (4.99 mmol, 1.0 eq.) in 7.5 ml of dry acetone, 770 µl of bromopyruvic ethyl ester (90%, 5.52 mmol, 1.1 eq.) is added dropwise at −10° C. After 1.5 h, the reaction mixture is poured with vigorous stirring into a mixture of dichloromethane and saturated KHCO$_3$ solution (25 ml each), and the aqueous phase is extracted with dichloromethane. The combined organic phase are dried over Na$_2$SO$_4$, and the dichloromethane is removed with a rotary evaporator.

The hydroxythiazoline intermediate is dissolved in 6 ml of dry dichloromethane and admixed with 890 µl of pyridine (11.0 mmol, 2.2 eq.) at −20° C., followed by adding 1.05 ml of trifluoroacetic anhydride (5.49 mmol, 1.1 eq.) dropwise. The reaction mixture is heated at 0° C. within 2 hours and stirred at room temperature over night. It is diluted with dichloromethane and washed twice with saturated NaHCO$_3$ solution. The aqueous phase is extracted with dichloromethane, the combined organic phases are washed with 1 M KHSO$_4$ solution and dried over Na$_2$SO$_4$. After purification by column chromatography (8:2, 7:3, 1:1), the thiazole 2 is obtained as a yellow oil (1.56 g, 4.22 mmol, 84% of theory).

$R_f(2)=0.49$ (hexane:EE 1:1), 0.23 (hexane:EE 7:3)

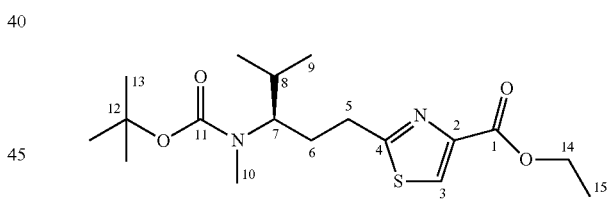

$^1$H NMR (400 MHz, CDCl$_3$): Ratio of rotamers at room temperature 54:46

1st rotamer: δ=0.83 (d, $^3J_{9,8}$=6.8 Hz, 3 H, 9-H), 0.93 (d, $^3J_{9',8}$=6.5 Hz, 3 H, 9'-H), 1.38 (t, $^3J_{15,14}$=7.2 Hz, 3 H, 15-H), 1.44 (s, 9 H, 13-H), 1.65 (m, 1 H, 8-H), 1.82 (m, 1 H, 6-H$_a$), 2.12 (m, 1 H, 6-H$_b$), 2.63 (s, 3 H, 10-H), 2.95 (t, $^3J_{5,6}$=8.1 Hz, 2H, 5-H), 3.82 (m, 1 H, 7-H), 4.40 (q, $^3J_{14,15}$=7.2 Hz, 2 H, 14-H), 8.03 (s, 1 H, 3-H).

2nd rotamer (the signals are in part below those of the 1st rotamer): δ=0.94 (d, $^3J_{9',8}$=6.8 Hz, 3 H, 9'-H), 1.38 (t, $^3J_{15,14}$=7.0 Hz, 3 H, 15-H), 1.41 (s, 9 H, 13-H), 2.68 (s, 3 H, 10-H), 2.94 (t, $^3J_{5,6}$=7.9 Hz, 2 H, 5-H), 3.63 (bs, 1 H, 7-H), 4.39 (q, $^3J_{14,15}$=7.0 Hz, 2 H, 14-H), 8.01 (s, 1 H, 3-H).

$^{13}$C NMR (100 MHz, CDCl$_3$):

1st rotamer: δ=14.4 (q, C-15), 19.6 (q, C-9), 19.9 (q, C-9'), 28.2 (q, C-10), 28.5 (q, C-13), 30.0 (t, C-6), 30.5 (d, C-8), 30.7 (t, C-5), 60.3 (d, C-7), 61.4 (t, C-14), 79.6 (s, C-12), 128.6 (d, C-3), 147.0 (s, C-2), 156.6 (s, C-11), 161.4 (s, C-1), 171.7 (s, C-4).

Selected signals of the 2nd rotamer: δ=20.1 (q, C-9), 20.3 (q, C-9'), 30.1 (t, C-6), 30.7 (t, C-5), 30.8 (d, C-8), 61.4 (t, C-14), 79.2 (s, C-12), 126.9 (d, C-3), 146.8 (s, C-2), 156.4 (s, C-11), 161.5 (s, C-1), 171.4 (s, C-4).

Optical rotation: $[\alpha]_D^{20}=-12.1°$ (c=1.0 g/100 ml, CHCl$_3$)

| HRMS (CI) | calculated | found |
|---|---|---|
| C$_{18}$H$_{31}$N$_2$O$_4$S [M + H]$^+$ | 371.2004 | 371.1964 |

1.6. (4S,2E)-4-(tert.-Butoxycarbonylamino)-2-methyl-5-phenyl-2-pentenic acid ethyl ester (8): To a solution of 4.90 g of L-Boc-phenylalanine methyl ester (17.5 mmol, 1.0 eq.) in 50 ml of absolute dichloromethane, 35 ml of a 1 M DIBAlH solution (35 mmol, 2.0 eq.) is added slowly dropwise at −78° C. While the reaction mixture is stirred at −78° C. for 30 min, the ylide solution is prepared from 15.5 g of (1-ethoxycarbonyl-ethyl)-triphenylphosphonium bromide (35.0 mmol, 2.0 eq.) and 4.03 g of KOtBu (35.9 mmol, 2.1 eq.) in 40 ml of absolute dichloromethane at room temperature. The ylide is added dropwise to the aldehyde solution at −78° C., and after one hour, the cooling bath is removed, and stirring is performed over night at room temperature.

The reaction mixture is poured into 800 ml of saturated potassium-sodium tartrate solution and stirred vigorously for 30 min. The aqueous phase is extracted with ethyl acetate, and the combined organic phases are dried over Na$_2$SO$_4$. Purification by column chromatography (hexane:EE 95:5, then 9:1) yields 4.78 g of the Wittig product (8) (14.3 mmol, 82% of theory) as a colorless oil, which congeals over night to give a white solid.

R$_f$(8)=0.31 (hexane:EE 8:2)

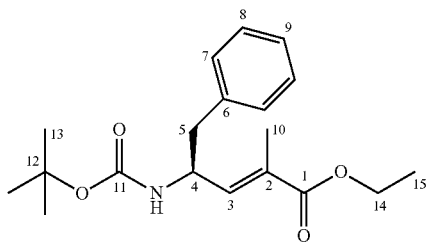 [SMILES: CCOC(=O)/C(C)=C/[C@H](Cc1ccccc1)NC(=O)OC(C)(C)C]

$^1$H NMR (500 MHz, CDCl$_3$): δ=1.26 (t, $^3J_{15,14}$=7.3 Hz, 3 H, 15-H), 1.38 (s, 9 H, 13-H), 1.68 (d, $^4J_{10,3}$=1.5 Hz, 3 H, 10-H), 2.76 (dd, $^2J_{5a,5b}$=13.3 Hz, $^3J_{5a,4}$=7.0 Hz, 1 H, 5-H$_a$), 2.90 (m, 1 H, 5-H$_b$), 4.16 (q, $^3J_{14,15}$=7.3 Hz, 2 H, 14-H), 4.55 (bs, 1 H, NH), 4.64 (bs, 1 H, 4-H), 6.49 (dd, $^3J_{3,4}$=9.1 Hz, $^4J_{3,10}$=1.5 Hz, 1 H, 3-H), 7.15 (d, $^3J_{7,8}$=7.0 Hz, 2 H, 7-H), 7.20 (t, $^3J_{9,8}$=7.3 Hz, 1 H, 9-H), 7.26 (dd, $^3J_{8,7}\approx{}^3J_{8,9}$=7.2 Hz, 2 H, 8-H).

$^{13}$C NMR (100 MHz, CDCl$_3$): δ=12.5 (q, C-10), 14.2 (q, C-15), 28.3 (q, C-13), 41.1 (t, C-5), 50.1 (d, C-4), 60.6 (t, C-14), 79.6 (s, C-12), 126.6 (d, C-9), 128.4 (d, C-8), 129.2 (s, C-2), 129.5 (d, C-7), 136.7 (s, C-6), 140.2 (d, C-3), 154.9 (s, C-11), 167.7 (s, C-1).

Melting point: 68° C.

1.7. (4S,2E)-4-(tert.-Butoxycarbonylamino)-2-methyl-5-phenyl-2-pentenic acid (9): A solution of 668 mg of (8) (2.00 mmol) in 20 ml of dioxan is admixed with 2.4 ml of 1 M NaOH solution (2.4 mmol, 1.2 eq.) at 0° C. Since the reaction has not proceeded to completion over night, the reaction mixture is heated at 80° C. for 2 hours. For processing, the dioxan is removed by rotary evaporation, the residue is taken up in water and extracted with ethyl acetate. The ethyl acetate phase is discarded, the aqueous phase is brought to pH 2 with 1 M HCl and extracted with ethyl acetate. The organic phase is dried over Na$_2$SO$_4$, and the solvent is removed on a rotary evaporator. 582 mg (1.91 mmol, 95% of theory) of the free acid 9 is isolated as a white solid.

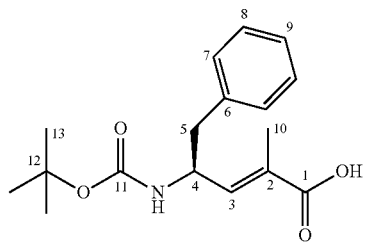 [SMILES: C/C(=C\[C@H](Cc1ccccc1)NC(=O)OC(C)(C)C)C(=O)O]

$^1$H NMR (400 MHz, CDCl$_3$): δ=1.39 (s, 9 H, 13-H), 1.66 (s, 3 H, 10-H), 2.76 (dd, $^2J_{5a,5b}$=13.1 Hz, $^3J_{5a,4}$=7.3 Hz, 1 H, 5-H$_a$), 2.92 (dd, $^2J_{5b,5a}$=13.1 Hz, $^3J_{5b,4}$=5.2 Hz, 1 H, 5-H$_b$), 4.53-4.73 (sh, 2 H, 4-H, NH), 6.63 (d, $^3J_{3,4}$=8.8 Hz, 1 H, 3-H), 7.15 (m, 2 H, 7-H), 7.21 (tt, $^3J_{9,8}$=7.3 Hz, $^4J_{9,7}$=1.5 Hz, 1 H, 9-H), 7.27 (dddd, $^3J_{8,7}\approx{}^3J_{8,9}$=7.2 Hz, $^4J_{8,8}\approx{}^5J_{8,7}$=1.5 Hz, 2 H, 8-H).

$^{13}$C NMR (100 MHz, CDCl$_3$): δ=12.2 (q, C-10), 28.3 (q, C-13), 41.0 (t, C-5), 50.3 (d, C-4), 79.8 (s, C-11), 126.8 (d, C-9), 128.5 (d, C-8), 129.5 (d, C-7), 136.5 (s, C-6), 142.6 (d, C-3), 172.5 (s, C-1).

The signal of C-2 cannot be seen.

Optical rotation: $[\alpha]_D^{20}=+44.9°$ (c=1.0 g/100 ml, CHCl$_3$)

Melting point: 138° C.

Elemental analysis:

| C$_{17}$H$_{23}$NO$_4$ | calc. | C | 66.86 | H | 7.59 | N | 4.59 |
|---|---|---|---|---|---|---|---|
| (305.37) | found | C | 66.55 | H | 7.57 | N | 4.45 |

| HRMS (CI) | calculated | found |
|---|---|---|
| C$_{17}$H$_{24}$NO$_4$ [M + H]$^+$ | 306.1705 | 306.1699 |

1.8. (4S,2E)-4-(tert.-Butoxycarbonylamino)-2-methyl-5-phenyl-2-pentenic acid [(1R,2S,5R)-(−)-menthyl]ester (10): To a solution of 657 mg of (9) (2.15 mmol), 840 mg of (−)-menthol (5.38 mmol, 2.5 eq.) and 26 mg of DMAP (0.213 mmol, 0.1 eq.) in 21.5 ml diethyl ether, 483 mg of DCC (2.34 mmol, 1.1 eq.) dissolved in 3 ml of diethyl ether is added at 0° C. The reaction mixture is allowed to warm to room temperature over night, the precipitated dicyclohexylurea is filtered off through Celite, and the filtrate is concentrated by rotary evaporation. Purification by column chromatography (hexane:EE 95:5) yields 690 mg of a white solid (1.56 mmol, 72% of theory).

R_f(10)=0.43 (hexane:EE 8:2)

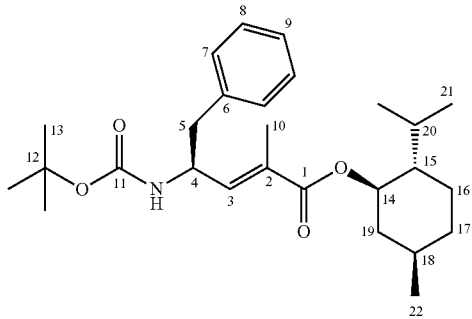 [SMILES: C/C(=C\[C@H](Cc1ccccc1)NC(=O)OC(C)(C)C)C(=O)O[C@@H]1C[C@H](C)CC[C@H]1C(C)C]

¹H NMR (400 MHz, CDCl₃): δ=0.74 (d, $^3J_{21,20}$=6.8 Hz, 3 H, 21-H), 0.85 (dddd, $^2J_{17ax,17eq}$≈$^3J_{17ax,16ax}$≈$^3J_{17ax,18(ax)}$=11.8 Hz, $^3J_{17ax,16eq}$=2.8 Hz, 1 H, 17-H$_{ax}$), 0.88 (d, $^3J_{22,18}$=6.3 Hz, 3 H, 22-H), 0.89 (d, $^3J_{21',20}$=6.8 Hz, 3 H, 21'-H), 0.93 (ddd, $^2J_{19ax,19eq}$≈$^3J_{19ax,18ax}$≈$^3J_{19ax,14(ax)}$=11.6 Hz, 1 H, 19-H$_{ax}$), 1.05 (dddd, $^2J_{16ax,16eq}$≈$^3J_{16ax,15(ax)}$≈$J_{16ax,17ax}$=12.9 Hz, $^3J_{16ax,17eq}$=3.0 Hz, 1 H, 16-H$_{ax}$), 1.39 (dddd, $^3J_{15(ax),14(ax)}$≈$^3J_{15(ax),16ax}$=10.0 Hz, $^3J_{15(ax),16eq}$≈$J_{15(ax),20}$=3.0 Hz, 1 H, 15-H$_{(ax)}$), 1.39 (s, 9 H, 13-H), 1.48 (m, 1 H, 18-H$_{(ax)}$), 1.63-1.71 (sh, 2 H, 16-H$_{eq}$, 17-H$_{eq}$), 1.69 (d, $^4J_{10,3}$=1.5 Hz, 3 H, 10-H), 1.83 (qqd, $^3J_{20,21}$=$^3J_{20,21'}$=6.8 Hz, $^3J_{20,15(ax)}$=2.8 Hz, 1 H, 20-H), 1.98 (m, 1 H, 19-H$_{eq}$), 2.77 (dd, $^2J_{5a,5b}$=13.3 Hz, $^3J_{5a,4}$=7.0 Hz, 1 H, 5-H$_a$), 2.91 (dd, $^2J_{5b,5a}$=13.3 Hz, $^3J_{5b,4}$=5.5 Hz, 1 H, 5-H$_b$), 4.54 (bs, 1 H, NH), 4.64 (bs, 1 H, 4-H), 4.68 (ddd, $^3J_{14(ax),15(ax)}$≈$J_{14(ax),19ax}$=10.8 Hz, $^3J_{14(ax),19eq}$=4.5 Hz, 1 H, 14-H$_{(ax)}$), 6.44 (dd, $^3J_{3,4}$=9.2 Hz, $^4J_{3,10}$=1.5 Hz, 1 H, 3-H), 7.12 (m, 2 H, 7-H), 7.19 (tt, $^3J_{9,8}$=7.3 Hz, $^4J_{9,7}$=1.9 Hz, 1 H, 9-H), 7.25 (dddd, $^3J_{8,7}$≈$^3J_{8,9}$=7.1 Hz, $^4J_{8,8'}$≈$^5J_{8,7'}$=1.8 Hz, 2 H, 8-H).

¹³C NMR (100 MHz, CDCl₃): δ=12.7 (q, C-10), 16.4 (q, C-21), 20.8 (q, C-21'), 22.0 (q, C-22), 23.5 (t, C-16), 26.4 (d, C-20), 28.3 (q, C-13), 31.4 (d, C-18), 34.3 (t, C-17), 40.9 (t, C-19), 41.2 (t, C-5), 47.2 (d, C-15), 50.0 (d, C-4), 74.5 (d, C-14), 79.7 (s, C-12), 126.7 (d, C-9), 128.4 (d, C-8), 129.6 (d, C-7), 139.6 (d, C-3), 154.9 (s, C-11), 167.1 (s, C-1).

The signal of C-2 cannot be seen.

Optical rotation: $[\alpha]_D^{20}$=−27.8° (c=1.0 g/100 ml, CHCl₃)
Melting point: 89-90° C.
Elemental analysis:

| C₂₇H₄₁NO₄ | calc. | C | 73.10 | H | 9.32 | N | 3.16 |
|---|---|---|---|---|---|---|---|
| (443.63) | found | C | 73.15 | H | 9.08 | N | 3.21 |
| HRMS (CI) | | calculated | | found | | | |
| C₂₇H₄₂NO₄ [M + H]⁺ | | 444.3114 | | 444.3077 | | | |

1.9. (2R,4R)- and (2S,4R)-4-(tert.-Butoxycarbonylamino)-2-methyl-5-phenyl-pentanoic acid [(1R,2S,5R)-(−)-menthyl]ester (11): Under a hydrogen atmosphere, 599 mg of (10) (1.35 mmol) dissolved in 13.5 ml of methanol is stirred with 60 mg of Pd/C (5%) until the reaction is complete (DC control). The catalyst is filtered off through Celite, and the filtrate is concentrated on a rotary evaporator.

In the NMR spectrum of the raw product, it can be seen that (epi-11) and (11) have been formed at a ratio of 1:3. After purification by column chromatography (hexane:Et₂O 9:1, hexane:EE 8:2), 89 mg of (epi-11) (0.200 mmol, 15% of theory), 361 mg of (11) (0.810 mmol, 60% of theory) and 121 mg of an (11)/(epi-11) mixed fraction (0.272 mmol, 20% of theory) can be isolated.

R_f(epi-11)=0.42 (hexane:EE 8:2), R_f(11)=0.38 (hexane:EE 8:2)

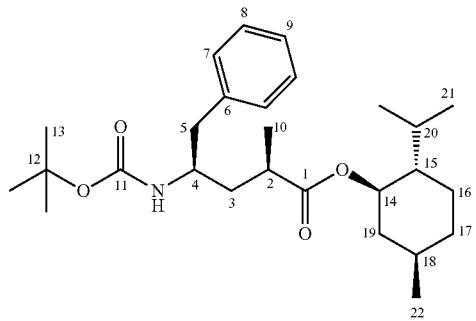 [SMILES: CC(C)[C@@H]1CC[C@@H](C)C[C@H]1OC(=O)[C@H](C)C[C@H](Cc1ccccc1)NC(=O)OC(C)(C)C]

¹H NMR (400 MHz, CDCl₃): δ=0.72 (d, $^3J_{21,20}$=6.8 Hz, 3 H, 21-H), 0.84 (dddd, $^2J_{17ax,17eq}$≈$^3J_{17ax,16ax}$≈$^3J_{17ax,18(ax)}$=12.9 Hz, $^3J_{17ax,16eq}$=3.6 Hz, 1 H, 17-H$_{ax}$), 0.86 (d, $^3J_{21',20}$=7.0 Hz, 3 H, 21'-H), 0.87 (d, $^3J_{22,18}$=6.5 Hz, 3 H, 22-H), 0.90 (ddd, $^2J_{19ax,19eq}$≈$^3J_{19ax,18ax}$≈$^3J_{19ax,14(ax)}$=11.8 Hz, 1 H, 19-H$_{ax}$), 1.02 (dddd, $^2J_{16ax,16eq}$≈$^3J_{16ax,15(ax)}$≈$J_{16ax,17ax}$=13.0 Hz, $^3J_{16ax,17eq}$=3.3 Hz, 1 H, 16-H$_{ax}$), 1.11 (d, $^3J_{10,2}$=7.3 Hz, 3 H, 10-H), 1.29-1.47 (sh, 2 H, 15-H$_{(ax)}$, 18-H$_{(ax)}$), 1.38 (s, 9 H, 13-H), 1.49 (ddd, $^2J_{3a,3b}$=14.2 Hz, $^3J_{3a,2/4}$=8.5 Hz, $^3J_{3a,2/4}$=4.0 Hz, 1 H, 3-H$_a$), 1.61-1.69 (sh, 2 H, 16-H$_{eq}$, 17-H$_{eq}$), 1.73 (ddd, $^2J_{3b,3a}$=14.2 Hz, $^3J_{3b,2/4}$=11.0 Hz, $^3J_{3b,2/4}$=5.5 Hz, 1 H, 3-H$_b$), 1.80 (ddd, $^3J_{20,21}$=$^3J_{20,21'}$=6.9 Hz, $^3J_{20,15(ax)}$=2.8 Hz, 1 H 20-H), 1.93 (m, 1 H, 19-H$_{eq}$), 2.44 (m, 1 H, 2-H), 2.73 (dd, $^3J_{5a,5b}$=13.5 Hz, $^3J_{5a,4}$=6.5 Hz, 1 H, 5-H$_a$), 2.79 (dd, $^2J_{5b,5a}$=13.5 Hz, $^3J_{5b,4}$=5.0 Hz, 1 H, 5-H$_b$), 3.87 (bs, 1 H, 4-H), 4.33 (d, $^3J_{NH,4}$=7.8 Hz, 1 H, NH), 4.62 (ddd, $^3J_{14(ax),15(ax)}$≈$^3J_{14(ax),19ax}$=10.9 Hz, $^3J_{14(ax),19eq}$=4.3 Hz, 1 H, 14-H$_{(ax)}$), 7.14 (d, $^3J_{7,8}$=7.0 Hz, 2 H, 7-H), 7.19 (tt, $^3J_{9,8}$=7.4 Hz, $^4J_{9,7}$=1.3 Hz, 1 H, 9-H), 7.26 (dddd, $^3J_{8,7}$≈$^3J_{8,9}$=7.2 Hz, $^4J_{8,8'}$≈$^5J_{8,7'}$=1.4 Hz, 2 H, 8-H).

¹³C NMR (100 MHz, CDCl₃): δ=16.2 (q, C-21), 16.8 (q, C-10), 20.8 (q, C-21'), 22.0 (q, C-22), 23.3 (t, C-16), 26.2 (d, C-20), 28.4 (q, C-13), 31.4 (d, C-18), 34.3 (t, C-17), 36.9 (d, C-2), 37.2 (t, C-3), 40.8 (t, C-19), 41.2 (t, C-5), 47.0 (d, C-15), 49.8 (d, C-4), 74.1 (d, C-14), 79.2 (s, C-12), 126.3 (d, C-9), 128.3 (d, C-8), 129.5 (d, C-7), 137.9 (s, C-6), 155.4 (s, C-11), 176.1 (s, C-1).

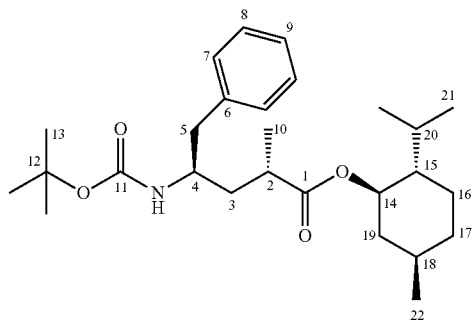 [SMILES: CC(C)[C@@H]1CC[C@@H](C)C[C@H]1OC(=O)[C@@H](C)C[C@H](Cc1ccccc1)NC(=O)OC(C)(C)C]

¹H NMR (400 MHz, CDCl₃): δ=0.72 (d, $^3J_{21,20}$=7.0 Hz, 3 H, 21-H), 0.84 (dddd, $^2J_{17ax,17eq}$≈$^3J_{17ax,16ax}$≈$^3J_{17ax,18(ax)}$=

12.9 Hz, $^3J_{17ax,16eq}$=3.5 Hz, 1 H, 17-$H_{ax}$), 0.87 (d, $^3J_{21',20}$=7.0 Hz, 3 H, 21'-H), 0.88 (d, $^3J_{22,18}$=6.5 Hz, 3 H, 22-H), 0.91 (ddd, $^2J_{19ax,19eq}$≈$^3J_{19ax,18ax}$≈$^3J_{19ax,14(ax)}$=11.7 Hz, 1 H, 19-$H_{ax}$), 1.03 (dddd, $^2J_{16ax,16eq}$≈$^3J_{16ax,15(ax)}$~$^3J_{16ax,17ax}$=13.0 Hz, $^3J_{16ax,17eq}$=3.4 Hz, 1 H, 16-$H_{ax}$), 1.13 (d, $^3J_{10,2}$=7.3 Hz, 3 H, 10-H), 1.30-1.54 (sh, 3 H, 3-$H_a$, 15-$H_{(ax)}$, 18-$H_{(ax)}$), 1.37 (s, 9 H, 13-H), 1.61-1.69 (sh, 2 H, 16-$H_{eq}$, 17-$H_{eq}$), 1.78-1.91 (sh, 2 H, 3-$H_b$, 20-H), 1.97 (d, $^2J_{19eq,19ax}$=11.5 Hz, 1 H, 19-$H_{eq}$), 2.54 (m, 1 H, 2-H), 2.75 (dd, $^2J_{5a,5b}$=13.2 Hz, $^3J_{5a,4}$=6.1 Hz, 1 H, 5-$H_a$), 2.79 (m, 1 H, 5-$H_b$), 3.85 (bs, 1 H, 4-H), 4.32 (bs, 1 H, NH), 4.65 (dddd, $^3J_{14(ax),15(ax)}$≈$^3J_{14(qx),19ax}$=10.9 Hz, $^3J_{14(ax),19eq}$=4.3 Hz, 1 H, 14-$H_{(ax)}$), 7.15 (d, $^3J_{7,8}$=7.3 Hz, 2 H, 7-H), 7.19 (tt, $^3J_{9,8}$=7.3 Hz, $^4J_{9,7}$=1.2 Hz, 1 H, 9-H), 7.26 (dddd, $^3J_{8,7}$≈$^3J_{8,9}$=7.3 Hz, $^4J_{8,8}$≈$^5J_{8,7'}$=1.3 Hz, 2 H, 8-H).

$^{13}$C NMR (100 MHz, CDCl$_3$): δ=16.1 (q, C-21), 17.7 (q, C-10), 20.8 (q, C-21'), 22.0 (q, C-22), 23.3 (t, C-16), 26.2 (d, C-20), 28.4 (q, C-13), 31.4 (d, C-18), 34.3 (t, C-17), 36.7 (d, C-2), 37.6 (t, C-3), 40.8 (t, C-19), 41.2 (t, C-5), 47.1 (d, C-15), 49.9 (d, C-4), 74.1 (d, C-14), 79.0 (s, C-12), 126.3 (d, C-9), 128.3 (d, C-8), 129.5 (d, C-7), 137.9 (s, C-6), 155.1 (s, C-11), 175.7 (s, C-1).

Optical rotation: [α]$_D^{20}$=−36.0° (c=1.0 g/100 ml, CHCl$_3$, epi-11)

[α]$_D^{20}$=−17.2° (c=1.0 g/100 ml, CHCl$_3$, 11)

Melting point: 110-111° C. (epi-11), 91-92° C. (11)

| HRMS (CI) | calculated | found |
|---|---|---|
| C$_{27}$H$_{44}$NO$_4$ [M + H]$^+$ | 446.3270 | 446.3280 |

1.10. (2S,4R)-4-Amino-2-methyl-5-phenyl-pentanoic acid methyl ester (3): The synthesis was performed as described in Zanda et al. (*Angew. Chem.* 2007, 119, 3596-3599). However, from 334 mg of (11) (0.750 mmol), only 138 mg of (3) (0.535 mg, 71% of theory) could be obtained (ref.: 99%).

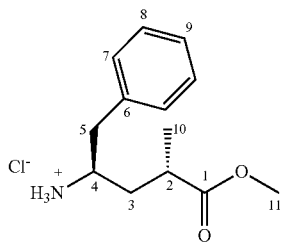 [SMILES: [Cl-] ; COC(=O)[C@@H](C)C[C@@H](N)Cc1ccccc1]

$^1$H NMR (400 MHz, CDCl$_3$): δ=1.13 (d, $^3J_{10,2}$=7.0 Hz, 3 H, 10-H), 1.78 (ddd, $^2J_{3a,3b}$=13.8 Hz, $^3J_{3a,2/4}$=8.9 Hz, $^3J_{3a,2/4}$=3.8 Hz, 1 H, 3-$H_a$), 1.97 (ddd, $^2J_{3b,3a}$=13.8 Hz, $^3J_{3b,2/4}$=10.7 Hz, $^3J_{3b,2/4}$=3.0 Hz, 1 H, 3-$H_b$), 2.90 (dd, $^2J_{5a,5b}$=13.6 Hz, $^3J_{5a,4}$=8.9 Hz, 1 H, 5-$H_a$), 2.92 (m, 1 H, 2-H), 3.27 (dd, $^2J_{5b,5a}$=13.6 Hz, $^3J_{5b,4}$=5.3 Hz, 1 H, 5-$H_b$), 3.58 (s, 3 H, 11-H), 3.60 (bs, 1 H, 4-H), 7.20-7.26 (sh, 3 H, 7-H, 9-H), 7.30 (dd, $^3J_{8,7}$≈$^3J_{8,9}$=7.2 Hz, 2 H, 8-H), 8.52 (bs, 3 H, NH$_3^+$).

$^{13}$C NMR (100 MHz, CDCl$_3$): δ=17.7 (q, C-10), 35.9 (d, C-2), 36.0 (t, C-3), 39.7 (t, C-5), 51.9 (q, C-11), 52.2 (d, C-4), 127.3 (d, C-9), 128.9 (d, C-8), 129.3 (d, C-7), 135.4 (s, C-6), 175.7 (s, C-1).

1.11. (R)-2-{3-[(N-Benzyloxycarbonyl-(S)-isoleucyl)-methylamino]-4-methyl-pentyl}-thiazole-4-carboxylic acid ethyl ester (12): 1.11 g of Boc-protected thiazole-amino acid (2) (3.00 mmol) is admixed with 7.5 ml of a 4 M HCl solution in dioxan (30.0 ml, 10 eq.) at 0° C. After complete removal of the Boc protecting group (DC control), the solvent is removed on a rotary evaporator. Subsequently, the hydrochloride salt as well as 876 mg of Z-L-isoleucine (3.30 mmol, 1.1 eq.) and 905 mg of BEP (3.30 mmol, 1.1 eq.) are dissolved in 30 ml of absolute CH$_2$Cl$_2$. At −10° C., 2.04 ml of DIPEA (12.0 mmol, 4.0 eq.) is added dropwise, and after 20 min, the cooling bath is removed, and the reaction mixture is stirred at room temperature over night. The solvent is removed on a rotary evaporator. Purification by column chromatography (hexane:EE 7:3, 1:1) yields 1.42 g of dipeptide (12) (2.64 mmol, 88% of theory) as a yellow oil.

R$_f$(12)=0.34 (hexane:EE 1:1)

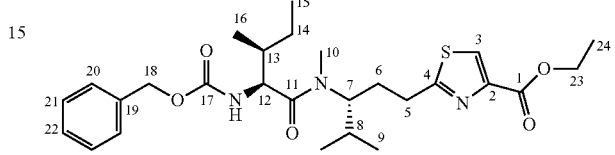

$^1$H NMR (400 MHz, CDCl$_3$):

Major rotamer: δ=0.75 (d, $^3J_{9,8}$=6.5 Hz, 3 H, 9-H), 0.86 (t, $^3J_{15,14}$=7.4 Hz, 3 H, 15-H), 0.95 (d, $^3J_{16,13}$=6.5 Hz, 3 H, 16-H), 0.96 (d, $^3J_{9',8}$=6.5 Hz, 3 H, 9'-H), 1.11 (ddq, $^2J_{14a,14b}$=13.6 Hz, $^3J_{14a,13}$=9.7 Hz, $^3J_{14a,15}$=7.3 Hz, 1 H, 14-$H_a$), 1.37 (t, $^3J_{24,23}$=7.0 Hz, 3 H, 24-H), 1.57 (dqd, $^2J_{14b, 14a}$=13.6 Hz, $^3J_{14b,15}$=7.6 Hz, $^3J_{14b,13}$=3.0 Hz, 1 H, 14-$H_b$), 1.63-1.79 (sh, 2 H, 8-H, 13-H), 1.88 (m, 1 H, 6-$H_a$), 2.14 (m, 1 H, 6-$H_b$), 2.83 (dt, $^2J_{5a,5b}$=15.2 Hz, $^3J_{5a,6}$=6.3 Hz, 1 H, 5-$H_a$), 2.89 (dt, $^2J_{5b,5a}$=15.2 Hz, $^3J_{5b,6}$=6.3 Hz, 1 H, 5-$H_b$), 2.94 (s, 3 H, 10-H), 4.32 (m, 1 H, 7-H), 4.39 (q, $^3J_{23,24}$=7.0 Hz, 1 H, 23-H), 4.52 (dd, $^3J_{12,NH}$=9.5 Hz, $^3J_{12,13}$=6.8 Hz, 1 H, 12-H), 5.05 (d, $^2J_{18a,18b}$=12.4 Hz, 1 H, 18-$H_a$), 5.08 (d, $^2J_{18b,18a}$=12.4 Hz, 1 H, 18-$H_b$), 5.40 (d, $^3J_{NH,12}$=9.5 Hz, 1 H, NH), 7.18-7.36 (sh, 5-H, arom. H), 8.01 (s, 1 H, 3-H).

Selected signals of the minor rotamer: δ=1.04 (d, $^3J_{9',8}$=6.8 Hz, 3 H, 9'-H), 2.23 (m, 1 H, 6-$H_a$), 2.74 (s, 3 H, 10-H), 3.58 (ddd, $^3J_{7,6a/b}$≈$^3J_{7,8}$=10.2 Hz, $^3J_{7,6a/b}$=3.3 Hz, 1 H, 7-H), 4.57 (dd, $^3J_{12,NH}$=9.6 Hz, $^3J_{12,13}$=6.3 Hz, 1 H, 12-H), 7.98 (s, 1 H, 3-H).

$^{13}$C NMR (100 MHz, CDCl$_3$):

Major rotamer: δ=11.2 (q, C-15), 14.3 (q, C-24), 16.0 (q, C-16), 19.5 (q, C-9), 20.0 (q, C-9'), 23.8 (t, C-14), 29.4 (q, C-10), 29.7 (t, C-6), 30.1 (d, C-8), 30.6 (t, C-5), 37.4 (d, C-13), 55.7 (d, C-12), 59.1 (d, C-7), 61.3 (t, C-23), 66.7 (t, C-18), 126.9 (d, C-3), 127.8 (d, C-20/21), 128.0 (d, C-22), 128.4 (d, C-20/21), 136.4 (t, C-19), 146.9 (s, C-2), 156.4 (s, C-17), 161.3 (s, C-1), 170.9 (s, C-4), 173.3 (s, C-11).

Selected signals of the minor rotamer: δ=11.3 (q, C-15), 16.1 (q, C-16), 20.3 (q, C-9), 20.4 (q, C-9'), 23.5 (t, C-14), 27.3 (q, C-10), 29.8 (t, C-6), 31.3 (t, C-5), 37.8 (d, C-13), 55.2 (d, C-12), 62.6 (d, C-7), 66.9 (t, C-18), 128.4 (d, C-20/21), 136.3 (t, C-19), 156.2 (s, C-17), 170.5 (s, C-4), 172.5 (s, C-11).

Optical rotation: [α]$_D^{20}$=−22.9° (c=1.0 g/100 ml, CHCl$_3$)

Elemental analysis:

| C$_{27}$H$_{39}$N$_3$O$_5$S | calc. | C | 62.64 | H | 7.59 | N | 8.12 |
|---|---|---|---|---|---|---|---|
| (517.68) | found | C | 62.30 | H | 7.61 | N | 8.24 |

| HRMS (CI) | calculated | found |
|---|---|---|
| C$_{27}$H$_{40}$N$_3$O$_5$S [M + H]$^+$ | 518.2689 | 518.2721 |

1.12. (R)-2-{3-[(N-Benzyloxycarbonyl-(R)-pipecolyl-(S)-isoleucyl)-methylamino]-4-methyl-pentyl}-thiazole-4-carboxylic acid ethyl ester (13): To 779 mg of the Z-protected dipeptide (12) (1.50 mmol), 2.59 ml of a 33% by weight HBr solution in glacial acetic acid (15 mmol, 10 eq.) is added at 0° C. After stirring for 2.5 h at room temperature, diethyl ether is added to the reaction mixture to precipitate the hydrobromide formed as an orange solid. The ether is removed by decantation, and the residue is again admixed with ether. This procedure is repeated twice. To obtain the free amine for further reaction, the hydrobromide is admixed with saturated NaHCO$_3$ solution, and the aqueous phase is repeatedly extracted with ether. The combined organic phases are dried over Na$_2$SO$_4$ and concentrated on a rotary evaporator.

To a solution of 434 mg of Z-(R)-pipecolinic acid (98.8% ee, 1.65 mmol, 1.1 eq.) and 198 µl of NMM (1.80 mmol, 1.2 eq.) in 15 ml of absolute THF, 214 µl of chloroformic acid isobutyl ester (1.65 mmol, 1.1 eq.) is added dropwise at −20° C. After 10 min, the amine, which has just been deprotected, is dissolved in 3 ml of absolute THF and added dropwise. The reaction mixture is allowed to warm to room temperature overnight. For processing, the precipitated NMM hydrochloride is filtered off, and the filtrate is concentrated by rotary evaporation. The residue is taken up in H$_2$O/EE, the aqueous phase is extracted with EE, and the combined organic phases are washed with saturated NaHCO$_3$ solution and dried over Na$_2$SO$_4$. After purification by column chromatography (hexane:EE 6:4, 1:1, 3:7), 720 mg of the product (13) (1.15 mmol, 76% of theory) is obtained as a white foam.

R$_f$(13)=0.18 (hexane:EE 1:1)

C-29), 67.6 (t, C-24), 126.9 (d, C-3), 127.8 (d, C-26/27), 128.0 (d, C-28), 128.5 (d, C-26/27), 136.3 (s, C-25), 146.9 (s, C-2), 156.4 (s, C-23), 161.3 (s, C-1), 170.3 (s, C-17), 170.8 (s, C-4), 173.2 (s, C-11).

Selected signals of the minor rotamer: δ=11.2 (q, C-15), 15.2 (q, C-30), 16.2 (q, C-16), 20.3 (q, C-9), 20.5 (q, C-9'), 23.4 (t, C-14), 27.4 (q, C-10), 29.9 (d, C-8), 31.3 (t, C-5), 53.0 (d, C-12), 61.3 (t, C-29), 62.7 (d, C-7), 67.5 (t, C-24), 126.9 (d, C-3), 146.8 (s, C-2), 171.0 (s, C-4/11/17).

Optical rotation: [α]$_D^{20}$=+3.8° (c=1.0 g/100 ml, CHCl$_3$)

| HRMS (CI) | calculated | found |
|---|---|---|
| C$_{33}$H$_{49}$N$_4$O$_6$S [M + H]$^+$ | 629.3373 | 629.3327 |

1.13. (R)-2-{3-[(N-Benzyloxycarbonyl-(R)-pipecolyl-(S)-isoleucyl)-methylamino]-4-methyl-pentyl}-thiazole 4-carboxylic acid (14): A solution of 554 mg of tripeptide (13) (0.881 mmol) in 8.8 ml of dioxan is admixed with 1.32 ml of 1 M NaOH (1.32 mmol, 1.5 eq.) at 0° C. and stirred until deprotection is complete (DC control). For processing, the dioxan is removed by rotary evaporation, the residue is taken up in water and extracted with ethyl acetate. The ethyl acetate phase is discarded, the aqueous phase is brought to pH 2 with 1 M HCl and extracted with ethyl acetate. The organic phase is dried over Na$_2$SO$_4$, and the solvent is removed on a rotary

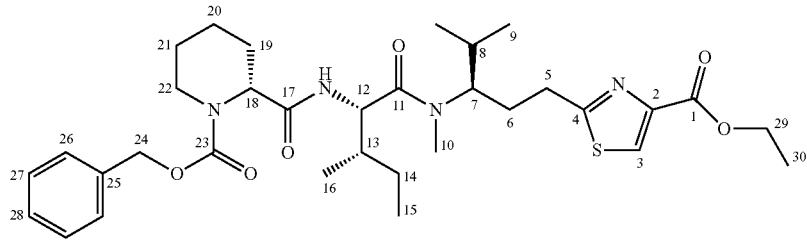 [SMILES: CCOC(=O)c1csc(CC[C@H](C(C)C)N(C)C(=O)[C@@H](NC(=O)[C@H]2CCCCN2C(=O)OCc2ccccc2)[C@@H](C)CC)n1]

$^1$H NMR (400 MHz, CDCl$_3$):

Major rotamer: δ=0.73 (d, $^3$J$_{9,8}$=6.8 Hz, 3 H, 9-H), 0.81 (m, 3 H, 15-H), 0.90 (m, 3 H, 16-H), 0.93 (d, $^3$J$_{9',8}$=6.8 Hz, 3 H, 9'-H), 1.01 (m, 1 H, 14-H$_a$), 1.25-1.41 (sh, 2 H, 20-H$_{ax}$, 21-H$_{ax}$), 1.36 (t, $^3$J$_{30,29}$=7.2 Hz, 3 H, 30-H), 1.41-1.63 (sh, 4 H, 14-H$_b$, 19-H$_{ax}$, 20-H$_{eq}$, 21-H$_{eq}$), 1.67 (m, 1 H, 8-H), 1.73 (m, 1 H, 13-H), 1.87 (m, 1 H, 6-H$_a$), 2.14 (m, 1 H, 6-H$_b$), 2.27 (d, $^2$J$_{19eq,19ax}$=12.8 Hz, 1 H, 19-H$_{eq}$), 2.77-2.86 (sh, 2 H, 5-H$_a$, 22-H$_{ax}$), 2.89 (ddd, $^2$J$_{5b,5a}$=15.1 Hz, $^3$J$_{5b,6a/b}$=6.2 Hz, $^3$J$_{5b,6a/b}$=3.3 Hz, 1 H, 5-H$_b$), 2.96 (s, 3 H, 10-H), 4.07 (bs, 1 H, 22-H$_{eq}$), 4.32 (m, 1 H, 7-H), 4.37 (q, $^3$J$_{29,30}$=7.2 Hz, 2 H, 29-H), 4.78 (dd, $^3$J$_{12,NH}$=$^3$J$_{12,13}$=8.3 Hz, 1 H, 12-H), 4.87 (bs, 1 H, 18-H), 5.11 (d, $^2$J$_{24a,24b}$=11.6 Hz, 1 H, 24-H$_a$), 5.15 (d, $^2$J$_{24b,24a}$=12.3 Hz, 1 H, 24-H$_b$), 6.55 (bs, 1 H, NH), 7.22-7.40 (sh, 5 H, arom. H), 8.00 (s, 1 H, 3-H).

Selected signals of the minor rotamer: δ=1.03 (d, $^3$J$_{9',8}$=6.3 Hz, 3 H, 9'-H), 2.73 (s, 3 H, 10-H), 3.61 (m, 1 H, 7-H), 4.17 (bs, 1 H, 22-H$_{eq}$), 4.92 (dd, $^3$J$_{12,NH}$=9.6 Hz, $^3$J$_{12,13}$=6.0 Hz, 1 H, 12-H), 5.06 (d, $^2$J$_{24a,24b}$=12.6 Hz, 1 H, 24-H$_a$), 7.95 (s, 1 H, 3-H).

$^{13}$C NMR (100 MHz, CDCl$_3$):

Major rotamer: δ=11.0 (q, C-15), 14.3 (q, C-30), 15.9 (q, C-16), 19.5 (q, C-9), 19.9 (q, C-9'), 20.4 (q, C-20), 24.1 (t, C-14), 24.7* (t, C-21), 25.9* (t, C-19), 29.3 (q, C-10), 29.7 (t, C-6), 30.1 (d, C-8), 30.6 (t, C-5), 37.1 (d, C-13), 42.2* (t, C-22), 53.6 (d, C-12), 55.2* (d, C-18), 58.9 (d, C-7), 61.3 (t, evaporator to obtain 518 mg of free acid (14) (0.862 mmol, 98% of theory) as a colorless glassy solid.

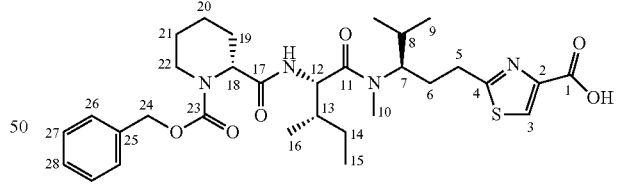

$^1$H NMR (400 MHz, CDCl$_3$):

Major rotamer: δ=0.74 (d, $^3$J$_{9,8}$=6.5 Hz, 3 H, 9-H), 0.81 (m, 3 H, 15-H), 0.88-0.98 (sh, 6 H, 9'-H, 16-H), 1.06 (m, 1 H, 14-H$_a$), 1.24-1.74 (sh, 7 H, 8-H, 14-H$_b$, 19-H$_{ax}$, 20-H, 21-H), 1.78-1.95 (sh, 2 H, 6-H$_a$, 13-H), 2.13 (m, 1 H, 6-H$_b$), 2.29 (d, $^2$J$_{19eq,19ax}$=13.3 Hz, 1 H, 19-H$_{eq}$), 2.83 (m, 1 H, 22-H$_{ax}$), 2.87 (t, $^3$J$_{5,6}$=7.8 Hz, 2 H, 5-H), 3.02 (s, 3 H, 10-H), 4.07 (bs, 1 H, 22-H$_{eq}$), 4.37 (m, 1 H, 7-H), 4.81 (dd, $^3$J$_{12,NH}$=$^3$J$_{12,13}$=8.7 Hz, 1 H, 12-H), 4.90 (bs, 1 H, 18-H), 5.12 (d, $^2$J$_{24a,24b}$=12.5 Hz, 1 H, 24-H$_a$), 5.17 (d, $^2$J$_{24b,24a}$=12.5 Hz, 1 H, 24-H$_b$), 6.85 (bs, 1 H, NH), 7.23-7.37 (sh, 5 H, arom. H), 8.10 (s, 1 H, 3-H).

Selected signals of the minor rotamer: δ=1.03 (d, $^3J_{9',8}$=6.5 Hz, 3 H, 9'-H), 2.73 (s, 3 H, 10-H), 3.64 (m, 1 H, 7-H), 4.14 (bs, 1 H, 22-H$_{eq}$), 6.95 (bs, 1 H, NH), 8.06 (s, 1 H, 3-H).

$^{13}$C NMR (100 MHz, CDCl$_3$):

Major rotamer: δ=10.8 (q, C-15), 15.8 (q, C-16), 19.5 (q, C-9), 19.9 (q, C-9'), 20.4 (t, C-20), 24.3 (t, C-14), 24.8* (t, C-21), 26.0* (t, C-19), 29.6 (t, C-6), 30.2 (d, C-8), 30.4 (t, C-5), 36.7* (d, C-13), 42.1* (t, C-22), 53.8 (d, C-12), 55.1* (d, C-18), 59.1 (d, C-7), 67.6 (t, C-24), 127.6, 127.8, 128.0 (3 d, C-26, C-27, C-28), 128.4 (d, C-3), 136.4 (s, C-25), 146.5 (s, C-2), 163.2 (s, C-1), 170.5 (s, C-5), 170.8 (s, C-17), 174.0 (s, C-11).

The signals of C-10 and C-23 cannot be seen.

Selected signals of the minor rotamer:

δ=11.2 (q, C-15), 16.1 (q, C-16), 20.2 (q, C-9), 20.5 (q, C-9'), 23.6 (t, C-14), 27.6 (q, C-10), 53.1 (d, C-12), 62.8 (d, C-7).

Optical rotation: [α]$_D^{20}$=+6.5° (c=1.0 g/100 ml, CHCl$_3$)
Melting point: 78-80° C.
Elemental analysis:

| C$_{31}$H$_{44}$N$_4$O$_6$S | calc. | C | 61.98 | H | 7.38 | N | 9.33 |
|---|---|---|---|---|---|---|---|
| (600.78) | found | C | 61.92 | H | 7.47 | N | 9.39 |

| HRMS (CI) | calculated | found |
|---|---|---|
| C$_{30}$H$_{45}$N$_4$O$_4$S [M − CO$_2$ + H]$^+$ | 557.3162 | 557.3186 |

1.14. (2S,4R)-4-[((R)-2-{3-[(N-Benzyloxycarbonyl-(R)-pipecolyl-(S)-isoleucyl)-me-thylamino]-4-methyl-pentyl}-thiazole-4-carbonyl)-amino]-2-methyl-5-phenyl-pentanoic acid methyl ester (15): To a solution of 120 mg of tripeptide (14) (0.200 mmol) and 24 µl of NMM (0.218 mmol, 1.1 eq.) in 2 ml of absolute THF, 28 µl of chloroformic acid iso-butyl ester (0.216 mmol, 1.1 eq.) is added dropwise at −20° C. After 10 min, the reaction mixture is admixed with another 24 µl of NMM (0.218 mmol, 1.1 eq.), followed by 57 mg of (3) (0.221 mmol, 1.1 eq.). The mixture is allowed to warm to room temperature over night.

For processing, the precipitated NMM hydrochloride is filtered off, and the filtrate is removed by rotary evaporation. The residue is taken up in H$_2$O/EE, the aqueous phase is extracted with EE, and the combined organic phases are washed with saturated NaHCO$_3$ solution and dried over Na$_2$SO$_4$. After purification by column chromatography (hexane:EE 1:1, 3:7), 129 mg of (15) (0.160 mmol, 80% of theory) is obtained as a colorless, highly viscous oil.

R$_f$(15)=0.19 (hexane:EE 1:1)

$^1$H NMR (400 MHz, CDCl$_3$):

Major rotamer: δ=0.76 (d, $^3J_{19,18}$=6.5 Hz, 3 H, 19-H), 0.82 (m, 3 H, 25-H), 0.92 (d, $^3J_{26,23}$=6.0 Hz, 3 H, 26-H), 0.95 (d, $^3J_{19',18}$=6.5 Hz, 3 H, 19'-H), 1.03 (m, 1 H, 24-H$_a$), 1.12 (d, $^3J_{10,2}$=7.0 Hz, 3 H, 10-H), 1.21-1.65 (sh, 7 H, 3-H$_a$, 24-H$_b$, 29H$_{ax}$, 30-H, 31-H), 1.66-1.91 (sh, 3 H, 16-H$_a$, 18-H, 23-H), 1.99 (ddd, $^2J_{3b,3a}$=13.5 Hz, $^3J_{3b,2/4}$=9.4 Hz, $^3J_{3b,2/4}$=4.0 Hz, 1 H, 3-H$_b$), 2.11 (m, 1 H, 16-H$_b$), 2.29 (d, $^2J_{29eq,29ax}$=12.8 Hz, 1 H, 29-H$_{eq}$), 2.58 (m, 1 H, 2-H), 2.69-3.02 (sh, 5 H, 5-H, 15-H, 32-H$_{ax}$), 2.98 (s, 3 H, 20-H), 3.59 (s, 3 H, 39-H), 4.08 (bs, 1 H, 32-H$_{eq}$), 4.29-4.44 (sh, 2 H, 4-H, 17-H), 4.80 (dd, $^3J_{22,NH}$≈$^3J_{22,23}$=8.0 Hz, 1 H, 22-H), 4.89 (bs, 1 H, 28-H), 5.11 (d, $^2J_{34a,34b}$=12.0 Hz, 1 H, 34-H$_a$), 5.16 (d, $^2J_{34b,34a}$=12.0 Hz, 1 H, 34-H$_b$), 6.56 (bs, 1 H, NH$_{Ile}$), 7.10-7.38 (sh, 11 H, arom. H, NH$_{Tup}$), 7.88 (s, 1 H, 13-H).

Selected signals of the minor rotamer: δ=1.05 (d, $^3J_{19',18}$=6.5 Hz, 3 H, 19'-H), 2.77 (s, 3 H, 20-H), 4.18 (bs, 1 H, 32-H$_{eq}$), 4.97 (dd, $^3J_{22,NH}$=9.0 Hz, $^3J_{22,23}$=7.0 Hz, 1 H, 22-H), 5.06 (d, $^2J_{34a,34b}$=12.6 Hz, 1 H, 34-H$_a$), 7.86 (s, 1 H, 13-H).

$^{13}$C NMR (100 MHz, CDCl$_3$):

Major rotamer: δ=11.0 (q, C-25), 15.8 (q, C-26), 17.7 (q, C-10), 19.6 (q, C-19), 20.0 (q, C-19'), 20.4 (t, C-30), 24.1 (t, C-24), 24.8* (t, C-31), 25.5* (t, C-29), 29.3 (t, C-16), 29.3* (q, C-20), 30.1 (t, C-15), 30.2 (d, C-18), 36.4 (d, C-2), 37.2 (d, C-23), 37.8 (t, C-3), 41.2 (t, C-5), 42.2* (t, C-32), 48.4 (d, C-4), 51.6 (q, C-39), 53.6 (d, C-22), 54.9* (d, C-28), 58.8* (d, C-17), 67.6 (t, C-34), 122.3 (d, C-13), 126.4 (d, C-9), 127.8 (d, C-36/37). 128.1 (d, C-38), 128.3 (d, C-8), 128.5 (d, C-36/37), 129.4 (d, C-7), 136.3 (s, C-35), 137.6 (s, C-6), 149.8 (s, C-12), 156.2* (s, C-33), 160.6 (s, C-11), 169.6 (s, C-14), 170.4 (s, C-27), 173.2 (s, C-21), 176.5 (s, C-1).

Selected signals of the minor rotamer: δ=11.2 (q, C-25), 16.2 (q, C-26), 20.3 (q, C-19), 20.5 (q, C-19'), 23.5 (t, C-24), 27.3 (q, C-20), 62.7 (d, C-17), 122.6 (d, C-13).

Optical rotation: [α]$_D^{20}$=+19.3° (c=1.0 g/100 ml, CHCl$_3$)

| HRMS (CI) | calculated | found |
|---|---|---|
| C$_{44}$H$_{62}$N$_5$O$_7$ [M + H]$^+$ | 804.4370 | 804.4331 |

1.15. (2S,4R)-4-[((R)-2-{3-[Methyl-(N-methyl-(R)-pipecolyl-(S)-isoleucyl)-amino]-4-methyl-pentyl}-thiazole-4-carbonyl)-amino]-2-methyl-5-phenyl-pentanoic acid methyl ester (16): To 114 mg of tetrapeptide (15) (0.142 mmol), 240 µl of HBr/AcOH (33% by weight, 1.39 mmol, 9.8 eq.) is added at 0° C. After stirring for 2 hours at room temperature, diethyl ether is added to the reaction mixture to precipitate the hydrobromide formed as an orange solid. The ether is

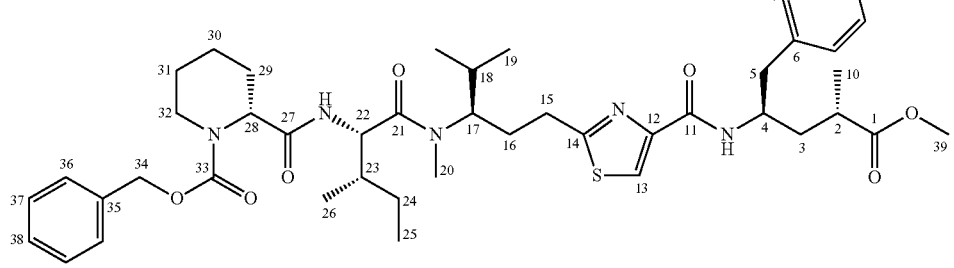

removed by decantation, and the residue is again admixed with ether. This procedure is repeated twice. To obtain the free amine for further reaction, The hydrobromide is admixed with saturated NaHCO$_3$ solution, and the aqueous phase is repeatedly extracted with ether. The combined organic phases are dried over Na$_2$SO$_4$ and concentrated on the rotary evaporator.

The free amine is dissolved in 1.4 ml of MeOH and preliminarily stirred with 12.8 mg of paraformaldehyde (0.142 mmol, 1.0 eq.) at room temperature for 45 min, whereupon 9.4 mg of sodium cyanoborohydride (0.150 mmol, 1.06 eq.) is added. After the reaction is complete (DC control, clear solution), The methanol is removed on a rotary evaporator, the residue is taken up in dichloromethane and washed with saturated NaHCO$_3$ solution. The aqueous phase is extracted with dichloromethane, and the combined organic phases are dried over Na$_2$SO$_4$. The raw product is purified by column chromatography (CH$_2$Cl$_2$:MeOH 99:1, 98:2, 95:5, 9:1) to obtain 64 mg of the product (16) (0.0936 mmol, 66% of theory) as a slightly yellowish oil.

R$_f$(16)=0.39 (CH$_2$Cl$_2$:MeOH 9:1)

$^1$H NMR (400 MHz, CDCl$_3$):

Major rotamer: δ=0.75 (d, $^3$J$_{19,18}$=6.5 Hz, 3 H, 19-H), 0.86 (t, $^3$J$_{25,24}$=7.4 Hz, 3 H, 25-H), 0.94 (d, $^3$J$_{19',18}$=6.5 Hz, 3 H, 19'-H), 0.96 (d, $^3$J$_{26,23}$=6.8 Hz, 3 H, 26-H), 1.08-1.25 (sh, 2 H, 24-H$_a$, 30-H$_{ax}$), 1.13 (d, $^3$J$_{10,2}$=7.3 Hz, 3 H, 10-H), 1.35 (ddd, $^2$J$_{29ax,29eq}$≈$^3$J$_{29ax,28}$≈$^3$J$_{29ax,30ax}$=12.1 Hz, 1 H, 29-H$_{ax}$), 1.43-1.72 (sh, 6 H, 3-H$_a$, 18-H, 24-H$_b$, 30-H$_{eq}$, 31-H), 1.74-1.91 (sh, 3 H, 16-H$_a$, 23-H, 29-H$_{eq}$), 1.94-2.03 (sh, 2 H, 3-H$_b$, 32-H$_{ax}$), 2.08 (dtd, $^2$J$_{16b,16a}$=14.5 Hz, $^3$J$_{16b,15}$=8.3 Hz, $^3$J$_{16b,17}$=3.6 Hz, 1 H, 16-H$_b$), 2.22 (s, 3 H, 33-H), 2.47 (d, $^3$J$_{28,29ax}$=9.0 Hz, 1 H, 28-H), 2.60 (m, 1 H, 2-H), 2.76-2.93 (sh, 4 H, 5-H$_a$, 15-H, 32-H$_{eq}$), 2.94 (dd, $^2$J$_{5b,5a}$=13.8 Hz, $^3$J$_{5b,4}$=6.0 Hz, 1 H, 5-H$_b$), 2.99 (s, 3 H, 20-H), 3.60 (s, 3 H, 34-H), 4.30-4.46 (sh, 2 H, 4-H, 17-H), 4.76 (dd, $^3$J$_{22,NH}$=9.3 Hz, $^3$J$_{22,23}$=8.3 Hz, 1 H, 22-H), 7.04 (bs, 1 H, NH$_{Ile}$), 7.15-7.27 (sh, 11 H, arom. H), 7.35 (d, $^3$J$_{NH,4}$=9.3 Hz, NH$_{Tup}$), 7.87 (s, 1 H, 13-H).

Selected signals of the minor rotamer: δ=0.87 (t, $^3$J$_{25,24}$=7.3 Hz, 3 H, 25-H), 1.06 (d, $^3$J$_{19',18}$=6.5 Hz, 3 H, 19'-H), 2.77 (s, 3 H, 20-H), 3.64 (m, 1 H, 17-H), 4.95 (dd, $^3$J$_{22,NH}$=9.7 Hz, $^3$J$_{22,23}$=6.2 Hz, 1 H, 22-H), 7.86 (s, 1 H, 13-H).

$^{13}$C NMR (100 MHz, CDCl$_3$):

Major rotamer: δ=11.0 (q, C-25), 15.9 (q, C-26), 17.8 (q, C-10), 19.6 (q, C-19), 20.1 (q, C-19'), 23.2 (t, C-30), 24.6 (t, C-24), 25.1 (t, C-31), 29.4 (t, C-16), 29.3* (q, C-20), 30.0 (t, C-15), 30.2 (d, C-18), 30.4 (t, C-29), 36.5 (d, C-2), 37.2 (d, C-23), 37.8 (t, C-3), 41.4 (t, C-5), 44.9 (q, C-33), 48.5 (d, C-4), 51.6 (q, C-34), 53.0 (d, C-22), 55.4 (t, C-32), 58.5* (d, C-17), 69.7 (d, C-28), 122.2 (d, C-13), 126.4 (d, C-9), 128.3 (d, C-8), 129.5 (d, C-7), 137.7 (s, C-6), 149.9 (s, C-12), 160.7 (s, C-11), 169.6 (s, C-14), 173.2 (s, C-21), 174.3 (s, C-27), 176.6 (s, C-1).

Selected signals of the minor rotamer: δ=16.5 (q, C-26), 17.6 (q, C-10), 22.7 (t, C-30), 41.1 (t, C-5), 49.2 (d, C-4), 122.5 (d, C-13).

Optical rotation: [α]$_D^{20}$=+22.9° (c=1.0 g/100 ml, CHCl$_3$)

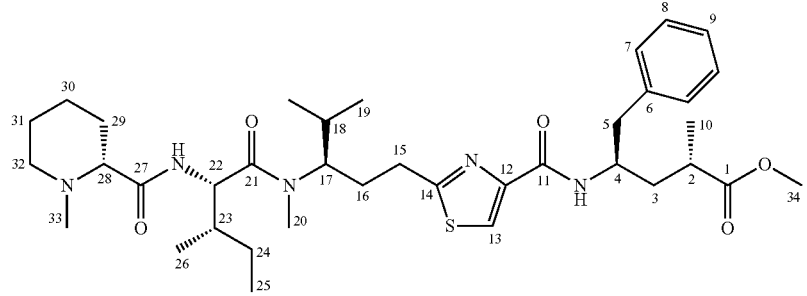 [SMILES: CC[C@H](C)[C@H](NC(=O)[C@H]1CCCCN1C)C(=O)N(C)[C@H](CCc1nc(C(=O)N[C@@H](Cc2ccccc2)C[C@H](C)C(=O)OC)cs1)C(C)C]

| HRMS (CI) | calculated | found |
|---|---|---|
| C$_{37}$H$_{58}$N$_5$O$_5$S [M + H]$^+$ | 684.4159 | 684.4153 |

1.16. (2S,4R)-4-[((R)-2-{3-[Methyl-(N-methyl-(R)-pipecolyl-(S)-isoleucyl)-amino]-4-methyl-pentyl}-thiazole-4-carbonyl)-amino-]-2-methyl-5-phenyl-pentanoic acid trifluoroacetic acid salt (1): A solution of 93 mg of the N-methylated tetrapeptide (16) (0.136 mmol) in 1.4 ml of dioxan is admixed with 270 µl of 1 M NaOH (0.27 mmol, 2.0 eq.) and heated at 80° C. for 3 hours. For processing, the dioxan is removed on the rotary evaporator, and the residue is taken up in water. The mixture is acidified to pH 1 with trifluoroacetic acid, and the product is extracted as a TFA salt with ethyl acetate. The combined organic phases are dried with Na$_2$SO$_4$ and subsequently concentrated. After purification by column chromatography (CH$_2$Cl$_2$:MeOH 9:1, 8:2), 1 is obtained in quantitative yield as a white solid.

$R_f(1)=0.11$ (CH$_2$Cl$_2$:MeOH 9:1)

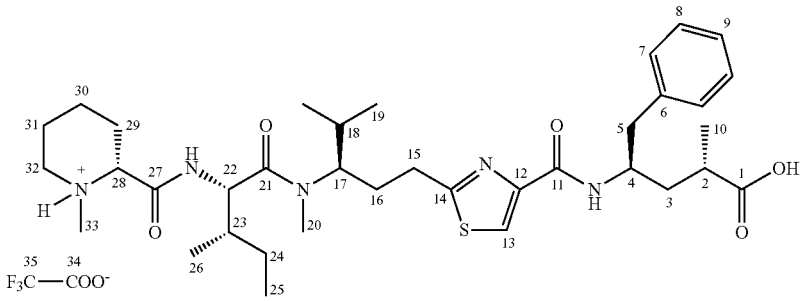

$^1$H NMR (400 MHz, MeOD):

Major rotamer: δ=0.81 (d, $^3J_{19,18}$=6.3 Hz, 3 H, 19-H), 0.93 (t, $^3J_{25,24}$=7.1 Hz, 3 H, 25-H), 0.99 (d, $^3J_{19',18}$=6.3 Hz, 3 H, 19'-H), 1.02 (d, $^3J_{26,23}$=6.5 Hz, 3 H, 26-H), 1.23 (m, 1 H, 24-H$_a$), 1.53-1.86 (sh, 6 H, 3-H$_a$, 18-H, 24-H$_b$, 29-H$_{ax}$, 30-H$_{ax}$, 31-H$_{ax}$), 1.86-2.08 (sh, 5 H, 3-H$_b$, 16-H$_a$, 23-H, 30-H$_{eq}$, 31-H$_{eq}$), 2.11-2.27 (sh, 2 H, 16-H$_b$, 29-H$_{eq}$), 2.56 (m, 1 H, 2-H), 2.74 (s, 3 H, 33-H), 2.81-3.02 (sh, 4 H, 5-H, 15-H), 3.09 (dd, $^2J_{32ax,32eq}$≈$^3J_{32ax,31ax}$=12.3 Hz, 1 H, 32-H$_{ax}$), 3.11 (s, 3 H, 20-H), 3.49 (d, $^2J_{32eq,32ax}$=11.5 Hz, 1 H, 32-H$_{eq}$), 3.76 (d, $^3J_{28,29ax}$=10.8 Hz, 1 H, 28-H), 4.24-4.47 (sh, 2 H, 4-H, 17-H), 4.70 (d, $^3J_{22,23}$=7.8 Hz, 1 H, 22-H), 7.16 (m, 1 H, 9-H), 7.19-7.29 (sh, 4 H, 7-H, 8-H), 7.95 (s, 1 H, 12-H).

Selected signals of the minor rotamer: δ=2.78 (s, 1 H, 20-H).

$^{13}$C NMR (100 MHz, MeOD, 5 k):

Major rotamer: δ=11.3 (q, C-25), 16.0 (q, C-26), 18.5 (q, C-10), 20.3 (q, C-19), 20.5 (q, C-19'), 22.3 (t, C-30), 24.0 (t, C-31), 25.5 (t, C-24), 30.2 (2 t, C-16, C-29), 30.3* (q, C-20), 30.9 (t, C-15), 31.4 (d, C-18), 37.5 (d, C-23), 37.9 (d, C-2), 39.2 (t, C-3), 42.4 (t, C-5), 42.9 (q, C-33), 50.7 (d, C-4), 56.0 (d, C-22), 56.2 (t, C-32), 60.6* (d, C-17), 68.1 (d, C-28), 118.2 (q, $^1J_{35,F}$=290.6 Hz, C-35), 124.0 (d, C-13), 127.4 (d, C-9), 129.3 (d, C-8), 130.4 (d, C-7), 139.5 (s, C-6), 150.5 (s, C-12), 163.1 (q, $^2J_{34,F}$=32.8 Hz, C-34), 163.1 (s, C-11), 169.2 (s, C-27), 171.9 (s, C-14), 174.6 (s, C-21), 180.0 (s, C-1).

Selected signals of the minor rotamer: δ=11.8 (q, C-25), 16.4 (q, C-26), 18.4 (q, C-10), 31.2 (d, C-18), 42.1 (t, C-5), 43.1 (q, C-33), 178.5 (s, C-1).

Optical rotation: $[\alpha]_D^{20}$=−17.1° (c=1.0 g/100 ml, CHCl$_3$)

Melting point: 60-62° C.

Example 2

Anti-proliferation Effects of Pre-tubulysins

Figure 1:
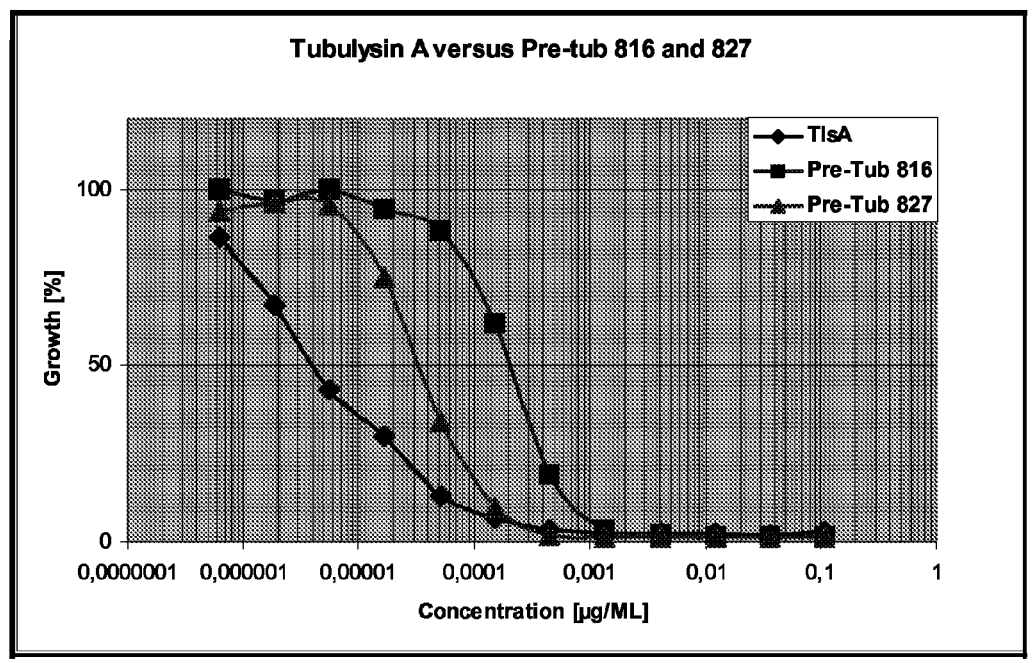
FIG. 1 shows the effect of pre-tubulysins 816 and 827 on the growth of HL-60 cells in comparison to tubulysin A.

To prove the expected anti-proliferative effects of pre-tubulysins the effect of different pre-tubulysins on the growth of HL-60 cell line was tested. A given number of cells were cultivated in 96-well plates with serial dilutions of the drugs up to 100 ng/ml. Tubulysin A is used as a positive control, whereas methanol is used as a negative control. After 5 days of incubation the metabolic activities of the cells were measured using MTT-assay as described under the methods section. Our results demonstrated that both pre-tubulysin-816 and -827 are able to inhibit the growth of the cells within this concentration range. However the cytotoxic activities were lower than that of tubulysin A under the same experimental conditions. The measured IC$_{50}$ values were 1.9, 17 and 150 pg/ml for tubulysin A, pre-tubulysin-827 and -816, respectively (FIG. 1).

In contrast, no anti-proliferation effects were observed for the other pre-tubulysin derivatives 814, 815 and 825 under the same experimental conditions and within the same concentration range (data not shown). To prove whether the 3 above mentioned derivatives are still inactive under higher concentrations, we repeated the Experiment under the same conditions, but at pre-tubulysin concentrations up to 11 μg/ml. The results are demonstrated in FIG. 2.

Figure 2:
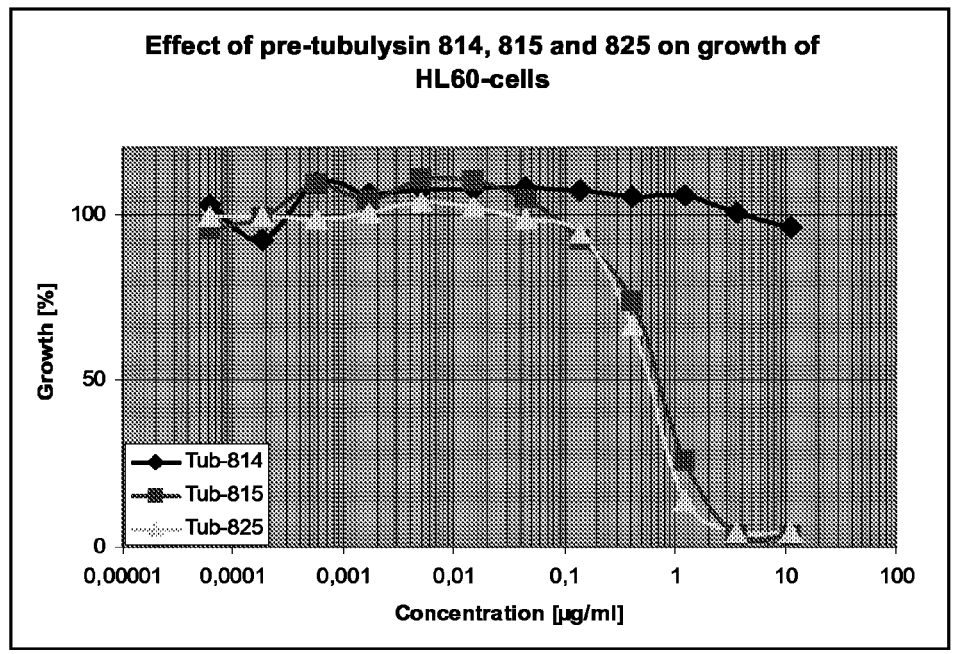
FIG. 2 shows the effect of pre-tubulysins-814, -815 and -825 on the growth of HL-60 cells.

As shown in FIG. 2, Pre-tubulysin-815 and -825 were active against HL-60 cells at higher concentrations. The measured IC$_{50}$-values for pre-tubulysin 815 and 825 were 700 and 600 ng/ml, respectively. Only pre-tubulysin-814 showed no cytotoxic activity, at concentration equal to or lower than 11 μg/ml.

The effect of pre-tubulysin 816 and 827 was tested with regard to the growth of other cell lines, including the mouse connective tissues fibroblast L929, the human lung carcinoma cell line A549, the human colon adenocarcinoma cell line SW-480, and the human histiocytic lymphoma cell line U937, in addition to the human myeloid leukemia cell line HL-60. The results are summarized in table one. Our results suggest that HL-60 and U937 cell lines are the most sensitive cell lines tested in our experiments. In contrast, the human lung carcinoma cell line showed (relatively) the lowest sensitivity to the pre-tubuluyins. Furthermore, pre-tubulysin-827 is approximately 5-10 folds more toxic than pre-tubulysin-816 (the IC$_{50}$ values of Tubulysin A in A549 and SW-480 cell lines could not be determined, because of the unusual high sensitivities of the two cell lines to the drug).

TABLE 1

Effects of pre-tubulyins -816 and -827 on the growth of different cell lines.

| | | | IC$_{50}$ value [ng/ml] | |
| | | | Pre- | Pre- |
| | | | Tub. | Tub. |
| Cell line | Origin | Tubulysin A | 816 | 827 |
| --- | --- | --- | --- | --- |
| L929 | mouse connective tissue fibroblast | 0.15 | 37 | 4.1 |
| A549 | human lung carcinoma | ND | 95 | 9 |
| SW-480 | human colon adenocarcinoma | ND | 1.37 | 0.15 |
| HL-60 | human acute myeloid leukemia | 0.002 | 0.15 | 0.017 |
| U937 | human histiocytic lymphoma | 0.002 | 0.4 | 0.09 |

(ND = not determined)

In summary, most of the tested pre-tubulysins were active against the tested cell lines. Only pre-tubulysin-814 didn't affect the growth of the treated cells at concentration up to 11 μg/ml. The most potent pre-tubulysin is pre-tubulysin-827. However the other pre-tubulins showed also considerable growth inhibition activities. The activity of the glycerolester of Pretubulyins is shown in FIG. 3.

Example 3

Effect of Pre-tubulysin-816 and -827 on the Morphologies of PtK2 Cells Microtubules Tubulysin A and D are known to induce de-polymerization of the interphase microtubules of mammalian cells and additionally induce a multi-polar spindle pool in mitotic cells (Khalil, M. et al., Chembiochem. 7, 678-683 (2006); Sasse, F., Menche, D. Nat. Chem. Biol. 3, 87-89 (2007)). Here the effect of pre-tubulysin treatment on the morphologies of microtubules and microtubules related structures in PtK2 cells was tested. PtK2 cells were seeded onto glass cover clips in 4 well plates and cultivated for 24 or 48 hours under growth conditions. The cells were then treated with different concentrations of tubulysin A, tubulysin D, pre-tubulysin-816 or pre-tubulysin-827. The control cells were treated only with equivalent amount of methanol (solvent). The cells were thin incubated for further 24 hours before they were fixed as described under the methods section. Fixed cells were then washed with PBS and finally labeled with anti-α-tubulin primary antibodies followed by anti-mouse-alexa-488 secondary antibodies to visualize the microtubules. The nuclei were stained with DAPI.

FIG. 4 shows the control cells with the normal morphology of the interphase microtubules, that look like thread like structures (FIG. 4A). The nuclei also show normal morphology (no fragmentations, and/or condensation). In addition FIG. 4B shows the normal morphology of the spindle pool in a cell during mitosis.

As shown in FIGS. 5A and 5B treatment of the cells with 50 pg/ml (FIG. 5A) Tubulysin D or 500 pg/ml tubulysin A (FIG. 5 B) induced a complete disappearance of the microtubules structures. Most of the nuclei of these cells are fragmented (data not shown).

Treatment of PtK2 cells with pre-tubulysin-816 with concentrations up to 250 ng/ml did not show any clear effect on the interphase microtubules. However, some mitosis cells showed abnormal spindle pools. The number of abnormal spindle apparatus increased clearly at concentrations equal to or higher than 500 ng/ml. Furthermore at these concentrations a different and characteristic morphology of the interphase microtubules could be also observed. The microtubules become denser around the periphery of the cell, and the length of the microtubules seemed shorter than the control cells. This morphologies are similar (but not identical) to that caused by some microtubules stabilizing agent (e.g. discodermolid). At concentration around 5 μg/ml the microtubules completely disappeared. Sometimes remain some florescence dots within the cytoplasm. FIG. 6 shows some of the above mentioned observations.

Similar observations could be also obtained after treatment the cells with pre-tubulysin-827. However, the effect on the microtubules and spindle pool morphologies began already at much lower concentrations (50 ng/ml) (FIG. 7). At concentrations equal to or greater than 1 μg/ml the microtubules become completely de-polymerized (FIG. 8).

The results suggest that Ptk2 Cells are in general less sensitive to pre-tubulysins than to tubulysin-A or -D. A complete de-polymerization of the interphase microtubules of PtK2 cells could first be observed after 24 hours incubations with 5 or 1 μg/ml of Pre-tubulysin-816 and -827, respectively. In comparison, 500 pg/ml tubulysin A or 50 pg/ml Tubulysin D were sufficient to induce equivalent morphological effects in PtK2 interphase microtubules after 24 hour of incubation. However, at concentrations lower than that needed for the complete de-polymerization of the interphase microtubules the 2 pre-tubulysins showed a unique effect on the microtubules, which is the formation of short and dense microtubules bundles near the nuclei as well as around the cell periphery. These characteristic morphologies are not previously observed after treatment the PtK2 cells with tubulysin A or tubulysin-D. Furthermore, similar effects are known to be caused by some microtubule stabilizing agents like discodermolide. However, the effects on the mitosis spindles are comparable to that caused by tubulysin A or D. The results suggest a different mechanism of action concerning the molecular interaction between pre-tubulysins and tubulin and/or microtubules protein. On the other side the results provide evidence that microtubles and tubulin are the cellular target of pre-tubulysins. However, the direct interaction between pre-tubulysin and tubulin had to be further investigated. To further investigate the effects of pre-tubulysins, we decided to test their effects on the tubulin polymerization in vitro.

As the immunofluorescence studies suggest that pre-tubulysins impair the formation and the stability of cell microtubules, we used a turbidometric assay to measure the effect of pre-tubulysins on the polymerization of purified microtubules protein isolated from porcine brain. 10 μM of purified microtubules protein were mixed on ice with 0, 1.7, 3.2, and 6.7 μM pre-tubulysin-816. Microtubules protein polymerization was then monitored for 10 min at 350 nm and 37° C. As shown in FIGS. 9 and 10, pre-tubulysin-816 was able to inhibit the polymerization of microtubules proteins in vitro at substoichiometric doses in a concentration-dependent manner. 1.7 μM of the drug was able to inhibit the polymerization of the protein by approximately 20%. Increase the concentration of the drug to 6.7 μM induced an inhibition of the polymerization to 60%.

Pre-tubulysin-827 was the most potent pre-tubulysin, in MTT-test as well as in the Immunofluorescence assay as demonstrated in the previous part of this report. Therefore, we were interested to test its activity on the polymerization of microtubules in vitro. We first studied its polymerization inhibition potential on microtubules polymerization. 10 μM of purified microtubules protein were mixed on ice with 0, 1, 1.7 and 3.4 μM pre-tubulysin-827 on ice. Microtubules protein polymerization was then monitored for 10 min at 350 nm and 37° C. The results are summarized in FIGS. 11 and 12.

AS expected, the inhibitory effect of pre-tubulysin-827 on the microtubules proteins polymerization in vitro was much higher than that of pre-tubulysin-816. 1 μM pre-tubulysin-827 was sufficient to inhibit the polymerization of 10 μM microtubules proteins by approximately 45%. Increasing the concentration of the drug to 3.4 μM induced a polymerization inhibition over 85%.

In order to examine the action of the drug on preassembled microtubules, microtubules proteins were firstly polymerized at 37° C. for approximately 5 min. Then the drug was added, and the stability of the microtubules was measured for further 10 min at 350 nm. As shown in FIG. 13, pre-tubulysin-827 induced de-polymerization of microtubules at substoichiometric concentrations. Similar effects could be also observed with pre-tubulysin-816 (data not shown).

In summary both pre-tubulysin-816 and -827 were able to inhibit the polymerization of microtubules proteins and also to induce the de-polymerization of preassembled microtubules in vitro at substoichiometric concentrations, whereby the effect of pre-tubulysin-827 is much higher that from pre-tubulysin-816. The efficacy of the first drug was comparable to that of tubulysin D (data not shown).

Example 4

Pre-tubulysins Induces a $G_2M$-Arrest in KB.3.1 Cells

All drugs that target the microtubules are known to induce a cell cycle arrest in $G_2M$ phase in different cell lines. The ability of pre-tubulysin-816 and -827 on the progress of cell cycle in the cervices carcinoma cell line KB.3.1 was tested. Cells were treated with different concentrations of the drugs and incubated for 24 hours under cultivation conditions. After the incubation time was ended, cells were collected by centrifugation, fixed and the DNA was labeled as described in the method sections. The DNA content of the cells was detected via FACS analysis. The resulting data were calculated using Dean-Jett-Fox algorithm.

As expected the two drugs were able to induce $G_2M$ cell cycle arrest in KB.3.1 cells. As shown in FIG. 14, pre-tubulysin-816 induced an accumulation of the cells in the $G_2M$-phase of the cell cycle. Similar results could be observed for pre-tublysin-827 (FIG. 15). However the cell cycle arresting effect could be observed at much lower concentration of the drug as shown in FIG. 15.

In Summary, both pre-tubulysin-816 and -827 induced a cell cycle arrest in KB3.1. This arrest is characterized by accumulation of the cells in $G_2M$ phase.

Example 5

Apoptosis Induction and DNA Laddering

Anti-mitotic agents like epothilone (Trivedi, M. et al., Future Oncol. 4, 483-500 (2008)) disorazol (Elnakady, Y. A. et al., Biochem. Pharmacol. 67, 927-935 (2004); Irschik, H. et al., Antibiot. (Tokyo) 48, 31-35 (1995)), and tubulysin (Khalil, M. et al., Chembiochem. 7, 678-683 (2006)) are known to induce apoptosis in different cancer cell lines. A hallmark of apoptosis induced by animitotic agent is the cleavage the chromosomal DNA into distinct fragments which can be separated via gel electrophoresis to give the so called DNA-Ladder. We tested the ability of pre-tubulysin-816 and -827 to induce apoptosis in HL-60 cell lines. Growing cells were treated with different concentrations of the drugs for 24 and 48 hours. After that cells were collected with centrifugation and the chromosomal DNA was separated by using agarose gel electrophoresis as described in the methods section. The resulting DNA bands were stained with ethidium bromide and visualized under UV-light. As shown in FIG. 16, both pre-tubulysin-816 and -827 were able to induce apoptosis in HL-60 cell line 24 hours after treatment. However, the concentration of Pre-tubulysin-816 that was needed to induce apoptosis in HL-60 cells was about 10 folds higher than that of pre-tubulysin-827 under the same experimental conditions. In Summary pre-tubulysins 816 and 827 are novel antimitotic drugs that target the microtubules, induce $G_2M$ arrest, and induce apoptosis in cancer cell lines. However, the molecular details of apoptosis induction caused by these Drugs is still to be investigated.

Example 6

Comparative Cytotoxicity Studies on Pretubulysins

Cytotoxicity testing of pretubulysin (AU827), N-desmethyl-pretubulysin (AU816) and Tubulysin A and D was performed as follows: Cells were seeded at $6 \times 10^3$ cells per well of 96-well plates in 180 µl complete medium and directly treated with varying concentrations of (pre-)tubulysins diluted in methanol. Each compound was tested in duplicate as well as the internal methanol control. After 5 d incubation, 20 µl of 5 mg/ml MTT (Thiazolyl blue tetrazolium bromide) in PBS was added per well and it was further incubated for 2 h at 37° C. The medium was then discarded and cells were washed with 100 µl PBS before adding 100 µl 2-propanol/10 N HCl (250:1) in order to dissolve formazan granules.

The absorbance at 570 nm was measured using a microplate reader (EL808, Bio-Tek Instruments Inc.), and cell viability was expressed as percentage relative to the respective methanol control. $IC_{50}$ values were obtained by plotting relative growth inhibition in % against the compound concentration on a logarithmic scale. After sigmoidal curve fitting $IC_{50}$ values can be determined. The $IC_{50}$[per ml] are shown in the following table (values represent the average of two measurements):

| cell line | origin | Tubulysin D | Tubulysin A | AU827 | AU816 |
| --- | --- | --- | --- | --- | --- |
| A431 | human (epithelial carcinoma) | 11.9 pg | 100.2 pg | 1.24 ng | 0.34 ng |
| A549 | human (lung carcinoma) | 5.6 pg | 85.6 pg | 4.35 ng | 31.2 ng |
| COS-7 | African green monkey (kidney carcinoma) | 33.7 pg | 80.6 pg | 1.13 ng | 9.63 ng |
| HEK293T | human (kidney) | 10.4 pg | 52.3 pg | 227.2 pg | 1.68 ng |
| HepG2 | human (hepatocellular carcinoma) | 6.6 pg | 120 pg | 0.64 ng | 8.75 ng |
| HL-60 | human (acute promyelocytic leukemia) | 2.8 pg | 47.9 pg | 14.2 ng | 0.22 ng |
| K562 | human (chronic myelogenous leukemia) | 22.2 pg | 0.40 ng | 0.35 ng | 2.5 ng |
| KB3.1 | human (cervical carcinoma) | 18.2 pg | 0.16 ng | 2.32 ng | 26.29 ng |
| L929 | mouse (subcutaneous connective tissue) | 17.0 pg | 0.21 ng | 3.87 ng | 39.95 ng |
| SH-SY5Y | human (neuroblastoma) | 11.3 pg | 0.21 ng | 0.61 ng | 2.9 ng |
| SW480 | human (colon adenocarcinoma) | 3.7 pg | 18.7 pg | 0.21 ng | 3.16 ng |
| U-2 OS | human (bone osteosarcoma) | 34.2 pg | 0.19 ng | 0.56 ng | 3.23 ng |
| U937 | human (histiocytic lymphoma) | 2.5 pg | 46.1 pg | 43.0 pg | 0.38 ng |

Similarly cytotoxicity testing of Pretubulysin-related compounds in U-2 OS human osteosarcoma cells was performed and was further compared with AU 339 and AU 954, compounds mentioned in WO2008/106080 and WO2004/046170. The $IC_{50}$ values are shown in the following table (values represent the average of two measurements):

| Compound | $IC_{50}$ [ng/ml] |
| --- | --- |
| Tubulysin D | 0.034 |
| Tubulysin A | 0.19 |
| AU827 | 0.56 |
| AU816 | 3.16 |
| AU954 | 82.0 |
| AU939 | 339.2 |

It is apparent that the compounds AU 816 and AU 827 of the present application possess activities comparable with that of tubulysin and superior than that of the prior art compounds.

Structures
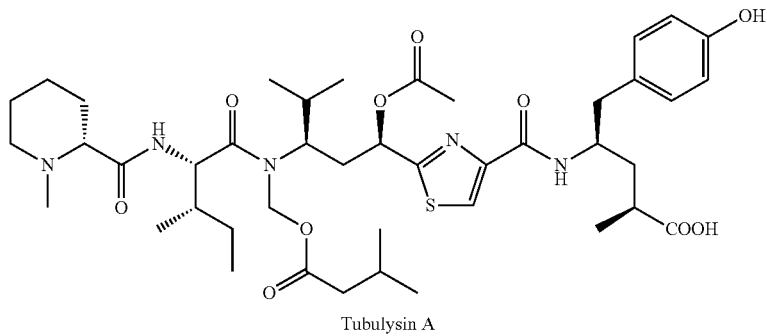
Tubulysin A
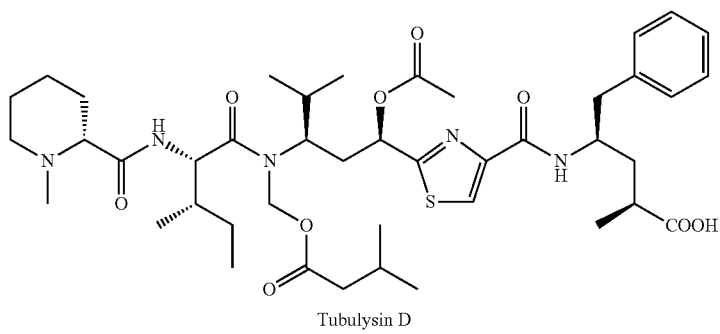
Tubulysin D
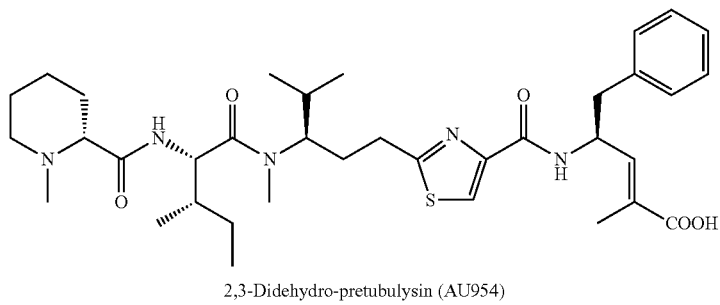
2,3-Didehydro-pretubulysin (AU954)
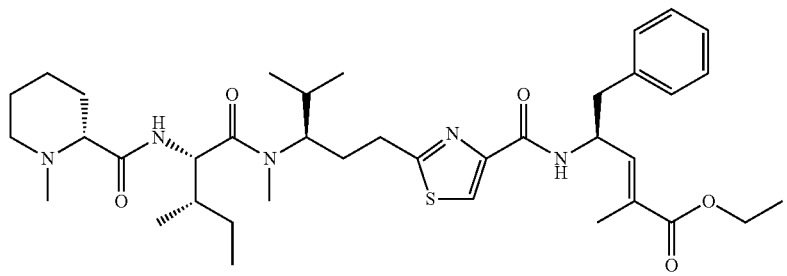
2,3-Didehydro-pretubulysin ethylester (AU939)

The invention claimed is:

1. A pre-tubulysin compound having the formula I or II

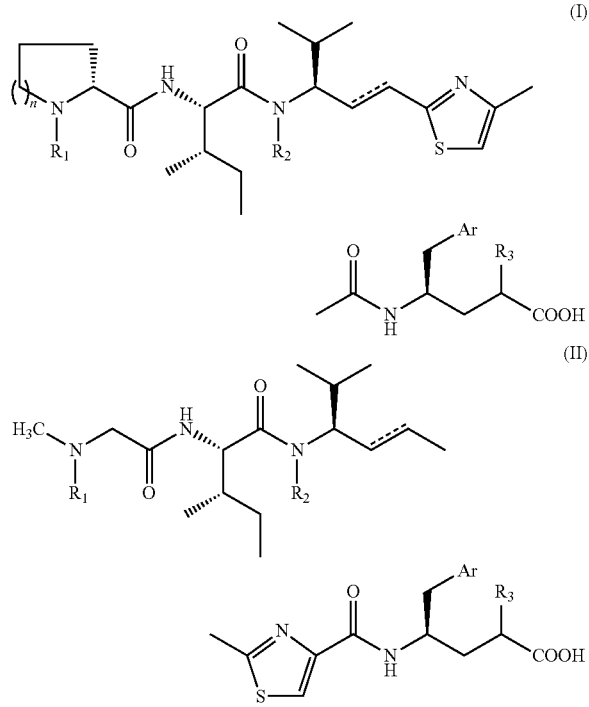

wherein $R_1$ is a branched or linear, saturated or unsaturated $C_{1-6}$ alkyl group which may carry 1 to 3 substituents independently selected from phenyl, halogen, $C_{1-3}$-alkoxy and phenoxy;

$R_2$ is a branched or linear, saturated or unsaturated $C_{1-16}$ alkyl group;

$R_3$ is H or a branched or linear, saturated or unsaturated $C_{1-6}$ alkyl group which may carry 1 to 3 substituents independently selected from phenyl, halogen, $C_{1-3}$-alkoxy and phenoxy;

Ar is phenyl or naphthyl group which may carry 1 to 3 substituents independently selected from $C_{1-3}$-alkyl, $C_{1-3}$-alkenyl, halogen, $C_{1-3}$-alkoxy and $C_{1-3}$-alkenoxy;

n is an integer of 0 to 2; and

------- denotes a single or double bond, or an ester of the C-terminal carboxy group with a monohydric or polyhydric alcohol and/or a pharmaceutically acceptable salt thereof.

2. The compound of claim 1, wherein $R_1$ is a methyl, ethyl, propyl, benzyl or allyl group; and/or $R_2$ is a $C_{1-12}$-alkyl group; and/or $R_3$ is H, a methyl, ethyl, allyl or benzyl group; and/or Ar is an unsubstituted phenyl group, a phenyl group substituted at the 4-position with the group X or a 2-naphthyl group substituted at the 6-position with the group X, wherein X is selected from —$CH_3$, —$OCH_3$, -allyl, -Oallyl and halogen; and/or n is 1 or 2; and/or ------- is a single bond.

3. The compound of claim 1 which has the structure I, wherein ------- is a single bond and (i) $R_1$, $R_2$ and $R_3$ are $CH_3$, Ar is an unsubstituted phenyl group, and n is 2, or (ii) $R_1$ and $R_2$ are $CH_3$, $R_3$ is H, Ar is an unsubstituted phenyl group, and n is 2, or a glycerolester thereof.

4. The compound of claim 1 which has the structure II, wherein ------- is a single bond, $R_1$ and $R_2$ are $CH_3$, $R_3$ is H, and Ar is an unsubstituted phenyl group, or a glycerolester thereof.

5. A pharmaceutical composition or medicament comprising the compound according to claim 1.

6. The pharmaceutical composition or medicament of claim 5, which is adapted for the treatment of cancer.

7. The compound of claim 1, wherein the monohydric or polyhydric alcohol is selected from the group consisting of $C_{1-6}$-alkanols, $C_{1-6}$-alkenols, $C_{2-6}$-alkylenediols and glycerol.

* * * * *

UNITED STATES PATENT AND TRADEMARK OFFICE
CERTIFICATE OF CORRECTION

PATENT NO. : 8,791,098 B2
APPLICATION NO. : 13/120497
DATED : July 29, 2014
INVENTOR(S) : Chai et al.

Page 1 of 1

It is certified that error appears in the above-identified patent and that said Letters Patent is hereby corrected as shown below:

In the specification

Column 5, line 21, "$C_{1\text{-}}$ -alkanols" -- should read -- $C_{1\text{-}6}$ -alkanols --.

Column 22, line 34, "ddd, $^3J$" -- should read -- qqd, $^3J$ --.

Column 22, line 36, "$^3J_{5a, 5b}$" -- should read -- $^2J_{5a, 5b}$ --.

Column 22, line 42, "$^4J_{8, 8'\sim}$" -- should read -- $^4J_{8, 8'\approx}$ --.

Column 23, line 4, "$^3J_{16ax, 15(ax)\sim}$" -- should read -- $^3J_{16ax, 15(ax)\approx}$ --.

Signed and Sealed this
Thirteenth Day of October, 2015

Michelle K. Lee
*Director of the United States Patent and Trademark Office*